(12) United States Patent
Ferdinand

(10) Patent No.: US 7,179,281 B2
(45) Date of Patent: Feb. 20, 2007

(54) HEALTH INDUSTRY MEDICAL NEOPRENE/LATEX COOLING GEL WRAP AROUND

(76) Inventor: Lester Ferdinand, 11822 SW. 100 Ter., Miami, FL (US) 33186

( * ) Notice: Subject to any disclaimer, the term of this patent is extended or adjusted under 35 U.S.C. 154(b) by 55 days.

(21) Appl. No.: 10/943,398

(22) Filed: Sep. 16, 2004

(65) Prior Publication Data

US 2006/0058860 A1    Mar. 16, 2006

(51) Int. Cl.
*A61F 7/00*    (2006.01)
(52) U.S. Cl. ....................... 607/108; 607/114
(58) Field of Classification Search ........ 607/108–112, 607/114
See application file for complete search history.

(56) References Cited

U.S. PATENT DOCUMENTS 6,440,159 B1 * 8/2002 Edwards et al. ............ 607/108
6,582,383 B2 * 6/2003 Horning ...................... 602/60

* cited by examiner

*Primary Examiner*—Roy D. Gibson
*Assistant Examiner*—Aaron Roane
(74) *Attorney, Agent, or Firm*—Carol N. Green

(57) ABSTRACT

This product will be used to help reduce/decrease, prevent and avoid swelling/edema to all joints and soft tissue areas of the body, which maybe as a result of surgery, athletic injury, slip and fall or systemic medical disorders.

The product will have a variety of specific body part covers, which will be provided in different sizes to address the injury in which the product is needed. The product will wrap around the body part and will hold together by Velcro. The product made of neoprene will have the capability to be placed in a 32 degree environment to turn the inner latex bag of liquid in to a cooling gel.

5 Claims, 44 Drawing Sheets

Cool Foot Toes Support

Cool Knee Support

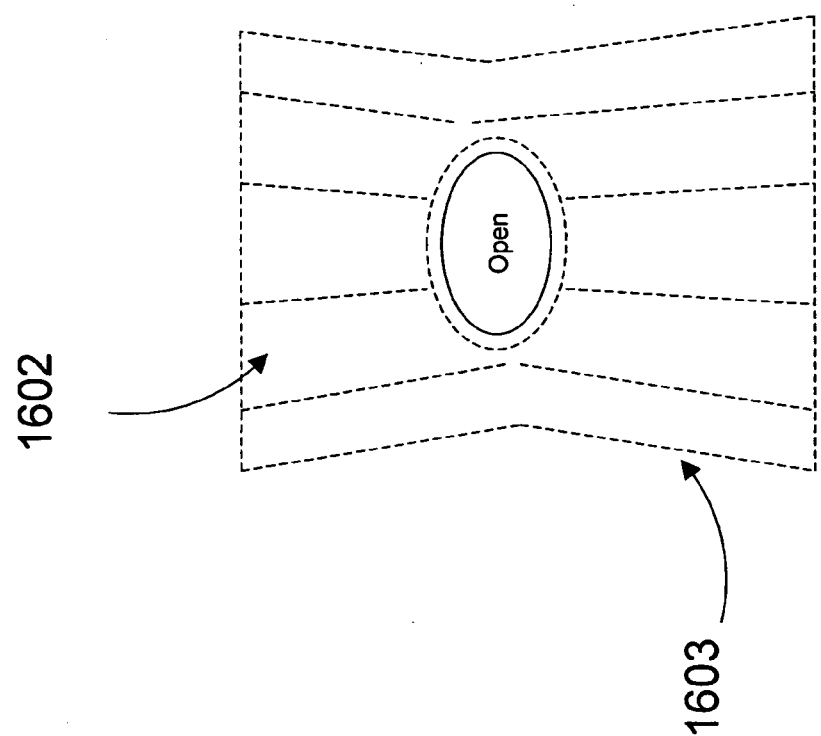
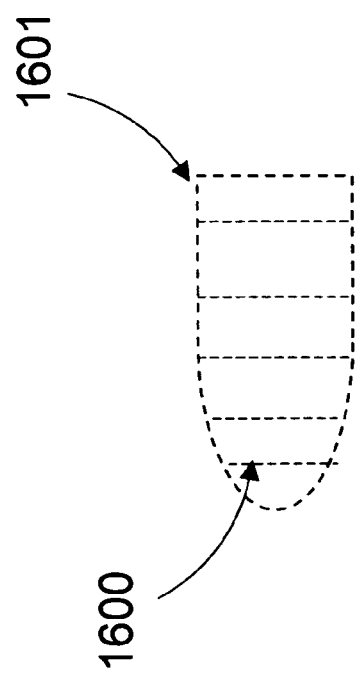
Fig 16

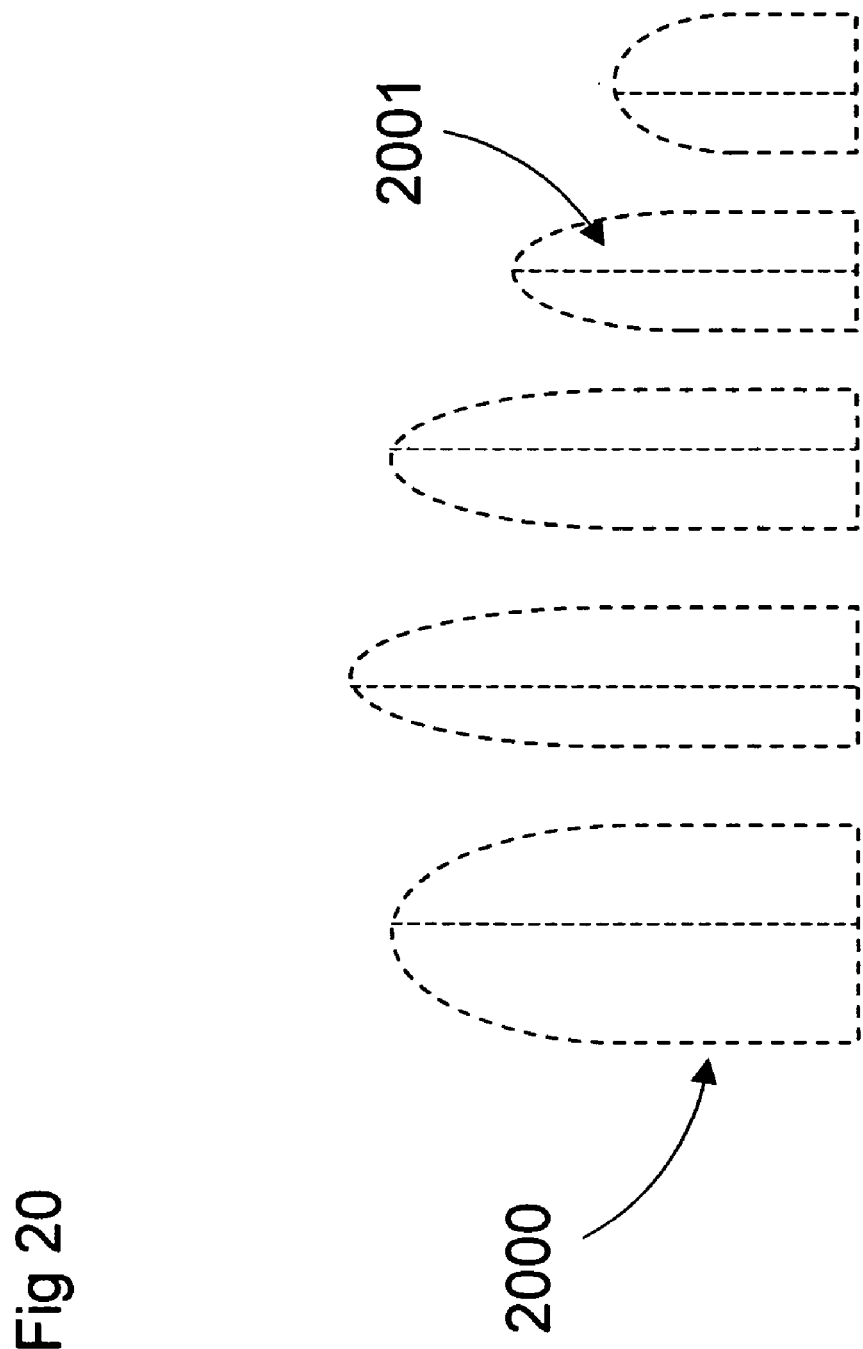

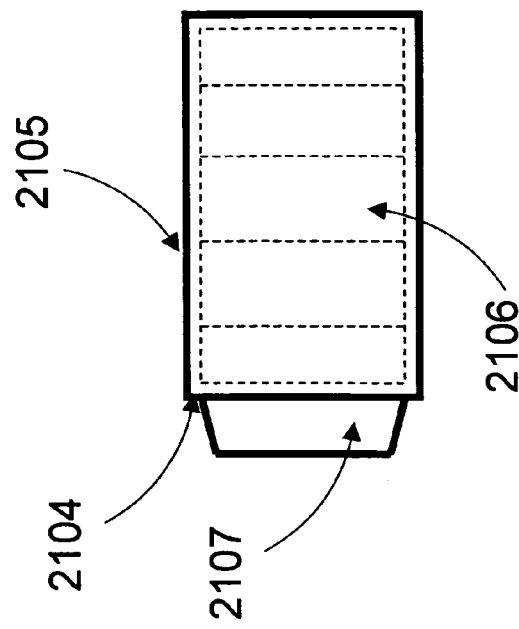
*Cool Calf Support*
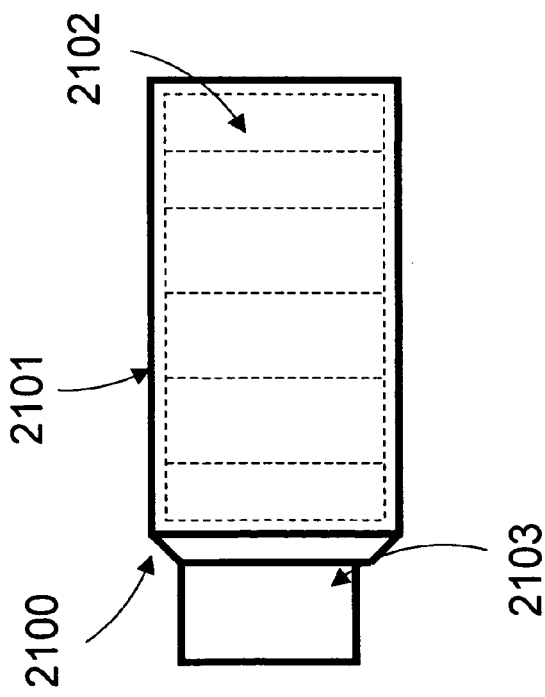
Fig 21  *Cool Thigh Support*

Fig 22
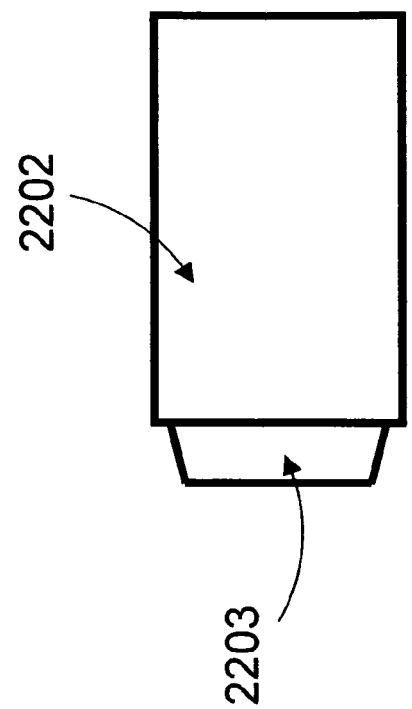
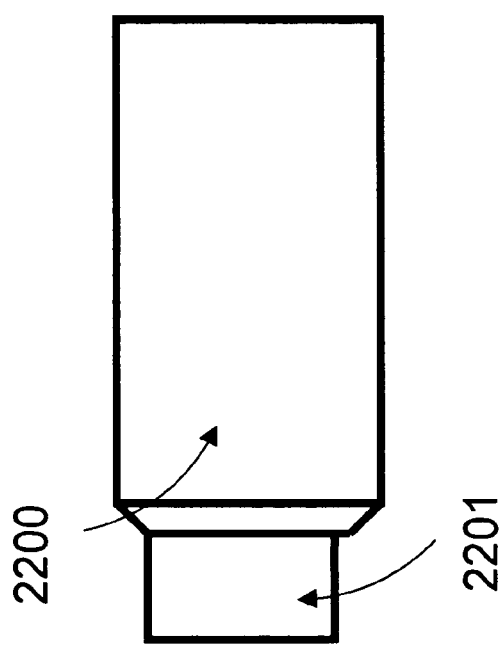

Cool Head & Face Support

Fig 29 — Cool Back Support

Cool Wrist Support

Cool Finger Support

HEALTH INDUSTRY MEDICAL NEOPRENE/LATEX COOLING GEL WRAP AROUND

BACKGROUND OF THE INVENTION

This product is designed for the health industry. It will be available to all health organizations: Hospitals, Doctors, Clinics, Pharmacies, Professional, Collegiate, and High School Athletic teams, and to everyone over the counter. This product will be used to help reduce/decrease, prevent and avoid swelling/edema to all joints and soft tissue areas of the body, which maybe may be as a result of surgery, athletic injury, slip and fall or systemic medical disorders.

SUMMARY OF THE INVENTION

An embodiment of the invention is a cooling system to help reduce/decrease, prevent and avoid swelling/edema to all joints and soft tissue areas of the body. The cooling system includes a chemical solution that can cool for up to 30 minutes. The product will fit a number of body parts: shoulders, back, head, feet, arms, neck, fingers, legs, toes and ankle.

Another embodiment of the invention is its ability to be put into a refrigeration device to cool the chemical solution into a gel. This flexible device is easily travelled friendly. Yet another embodiment of the invention is its ability to stretch and fit the body part needed for the cooling treatment. Cooling pockets help treat the body part needed.

BRIEF DESCRIPTION OF THE DRAWINGS

The present invention is illustrated by way of example and not limitation in the accompanying figures, in which like references indicate similar elements, and in which:

FIGS. 5–44 illustrate various perspectives of additional embodiments of the invention.

DETAILED DESCRIPTION OF THE DRAWINGS

Figure 1:
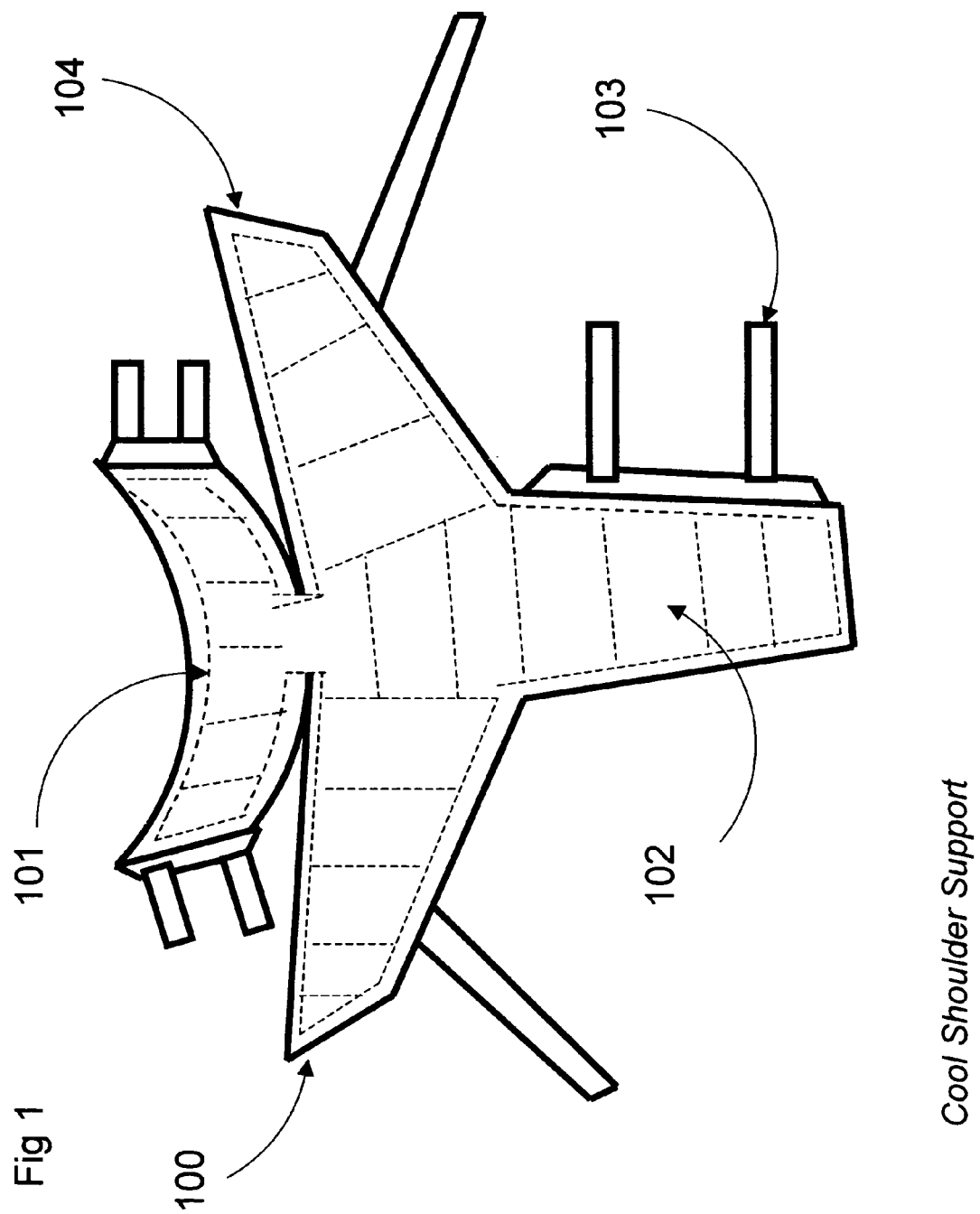
FIG. 1 illustrates a front, perspective view of a rehabilitation device, including a inner liner chemical gel, such as a cool pack providing reduction in swelling/edema in muscles and joints or other operations and functions, according to certain embodiments of the invention.

Referring to FIG. 1, a rehabilitation device cool gel shoulder 100, the cool gel shoulder 100 whieh includes an inner bag with 3 to 5 mm. thickness elements durability for use on swollen body parts, as rehabilitation support latex type material 102 cool gel substance. The rehabilitation device 103 shows elements of strapping type strips to keep the device together. Neoprene type material of 4 to 6 mm. thickness, 104 adds stretching to help contour to body parts.

Figure 2:
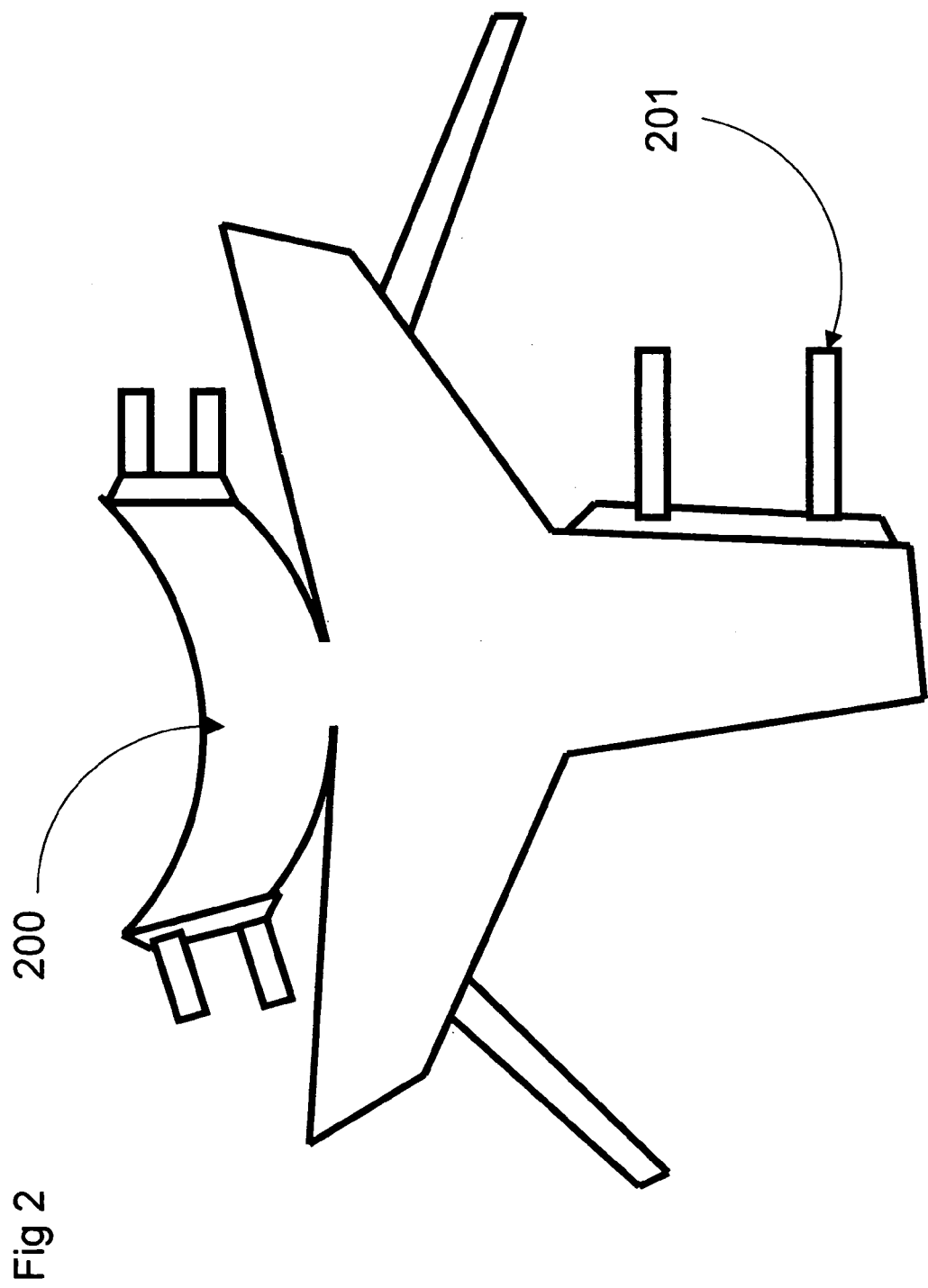
FIG. 2 illustrates a back, perspective view of the rehabilitation device of FIG. 1, showing the neoprene stretch type material and strapping components, according to certain embodiments of the invention.

Referring to FIG. 2, a back-side of the rehabilitation device 200 of FIG. 2 shows the back of the device. Neoprene type material of 4 to 6 mm. in thickness that stretches and forms to the body to give maximum support, 201 shows strapping straps to close and lock the device to the body parts.

Figure 3:
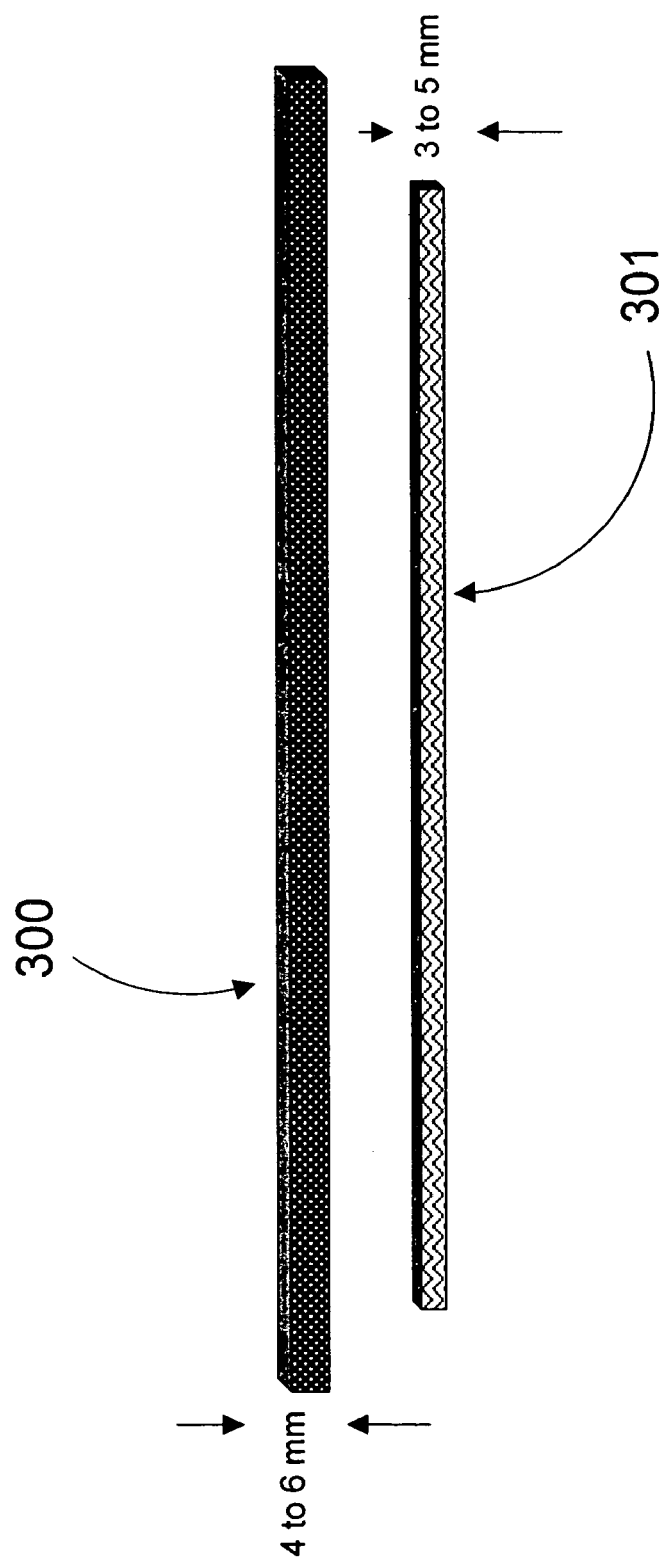
FIG. 3 illustrates a side perspective view rehabilitation device for providing particular layers and functionality, according to certain embodiments of the invention.

Referring to FIG. 3, an exemplary embodiment of the device illustrated in a simplified view for purposes of showing the material layers. 300 shows the Neoprene type material from the side view. The cooling packet 301 is also illustrated in side view.

Figure 4:
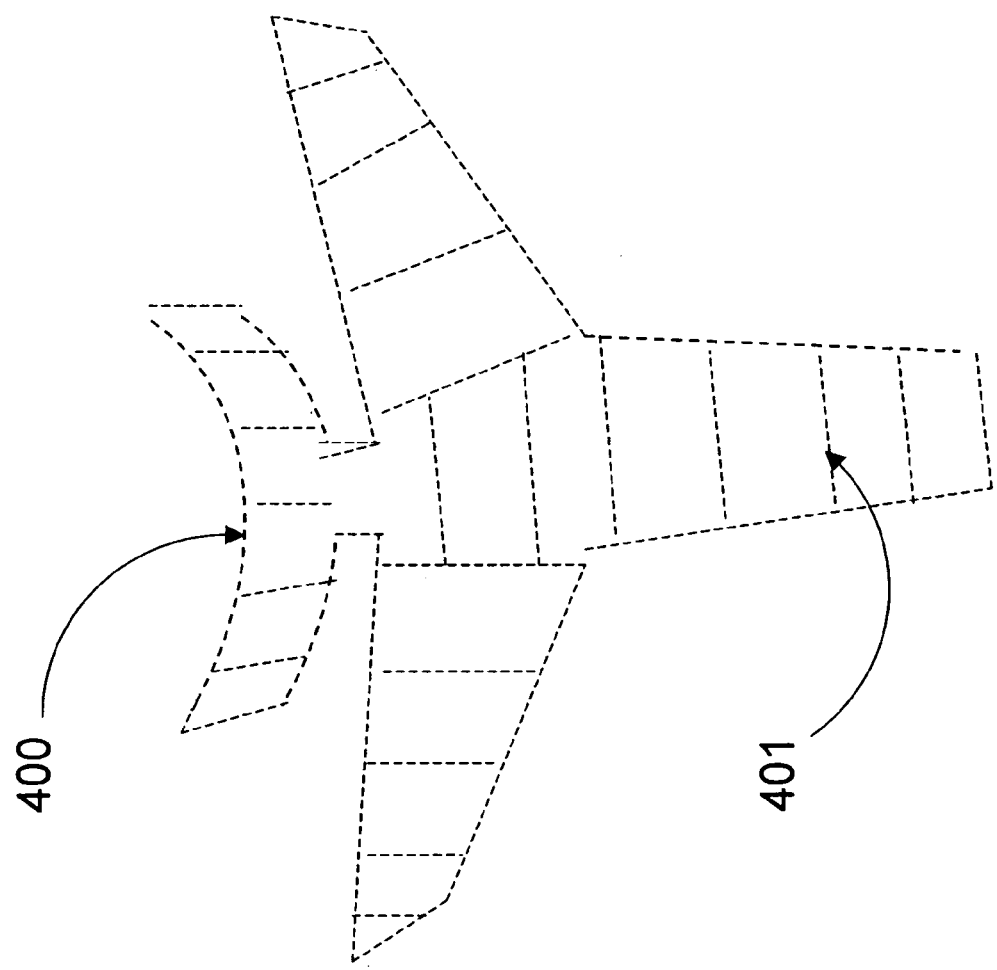
FIG. 4 illustrates a perspective of the gel pack, which provides cooling functional elements required for operations according to certain embodiments of the invention.
Figure 5:
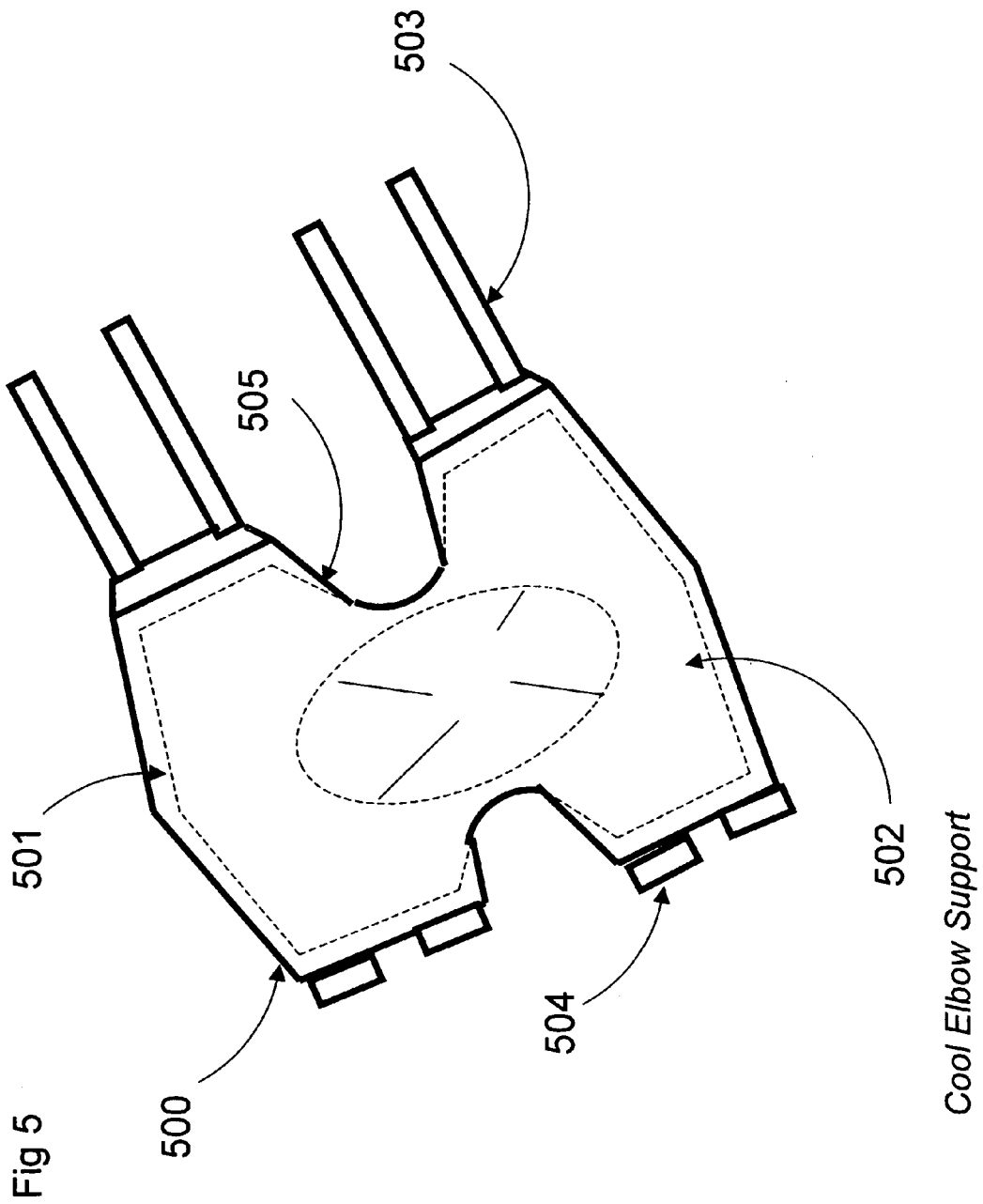
Figure 6:
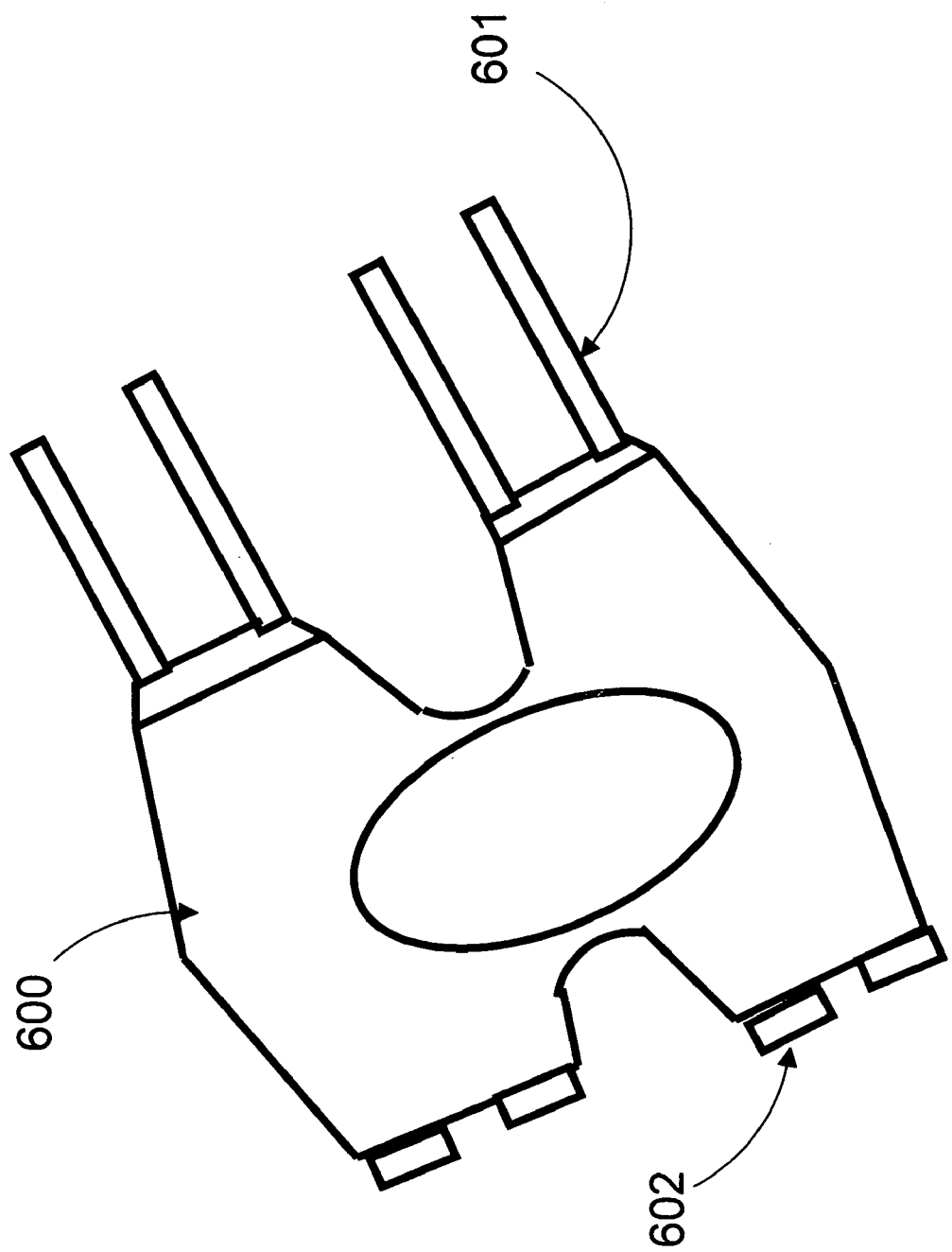
Figure 7:
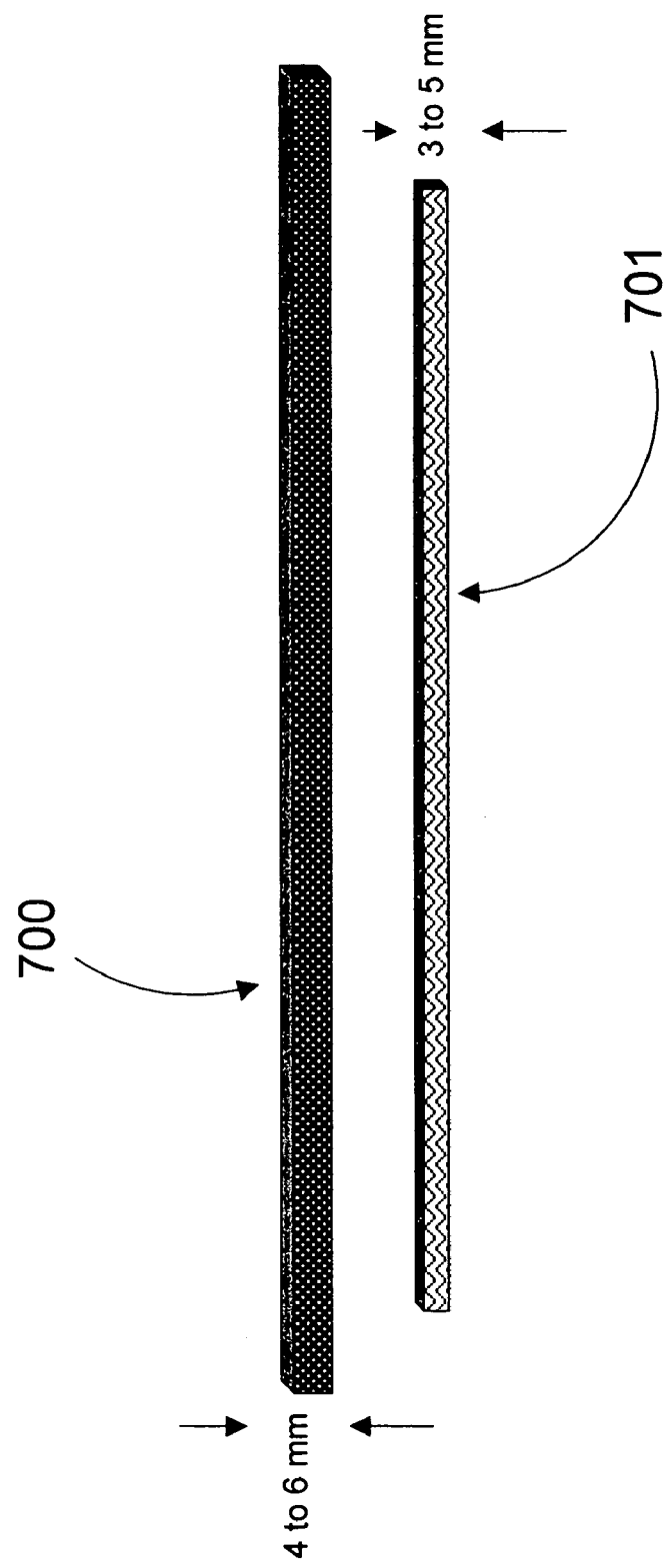
Figure 8:
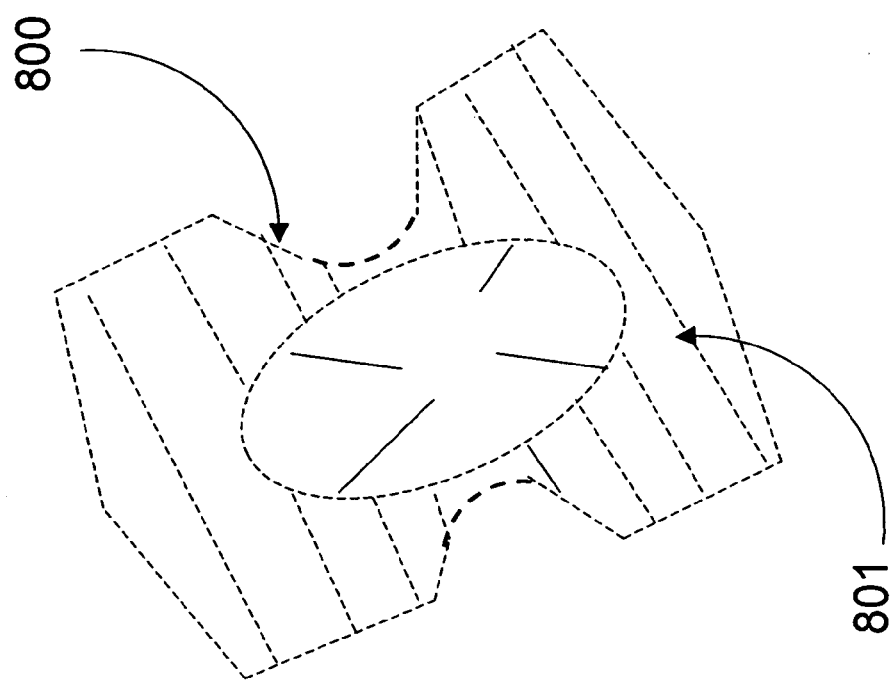
Figure 9:
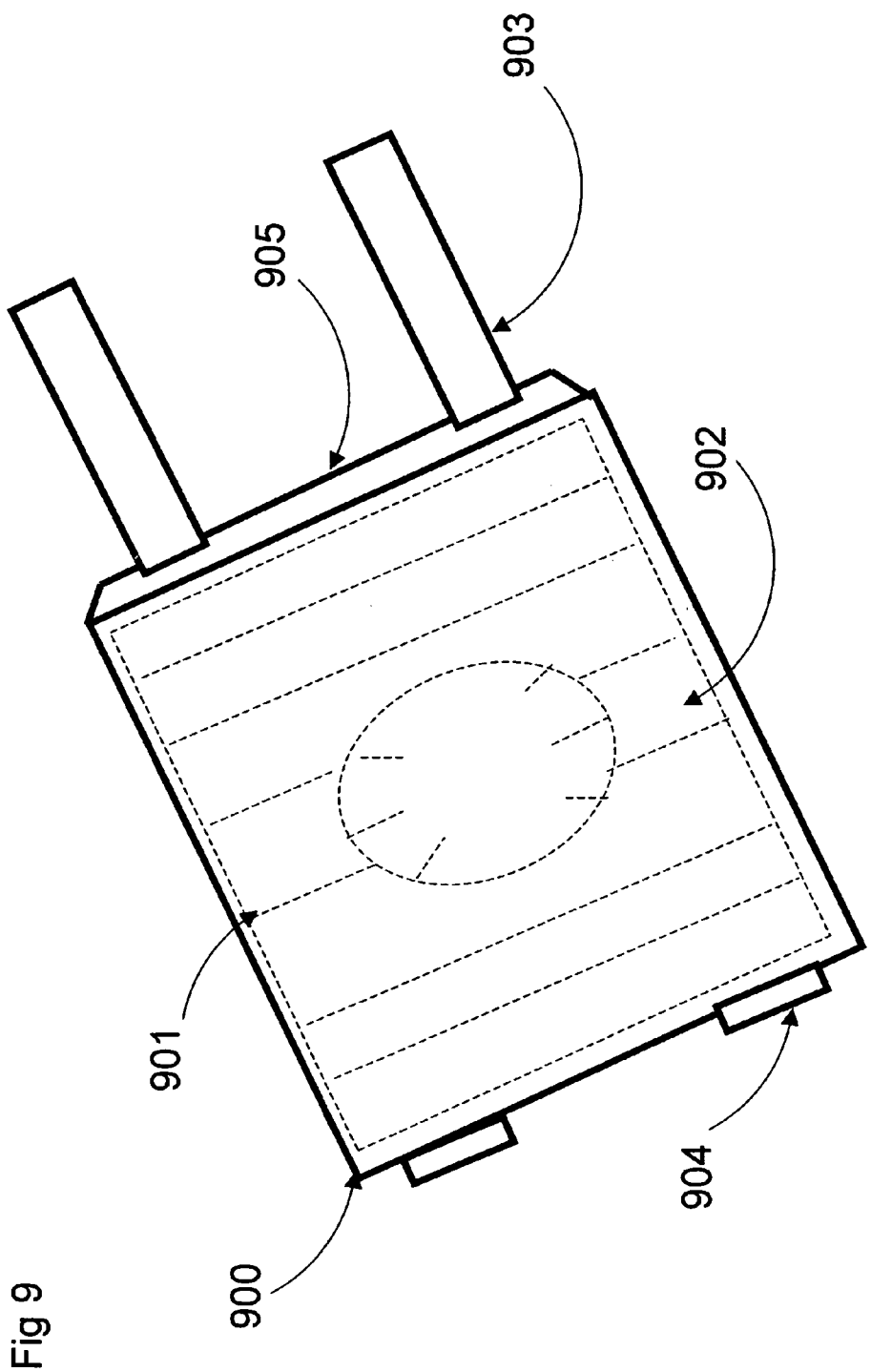
Figure 10:
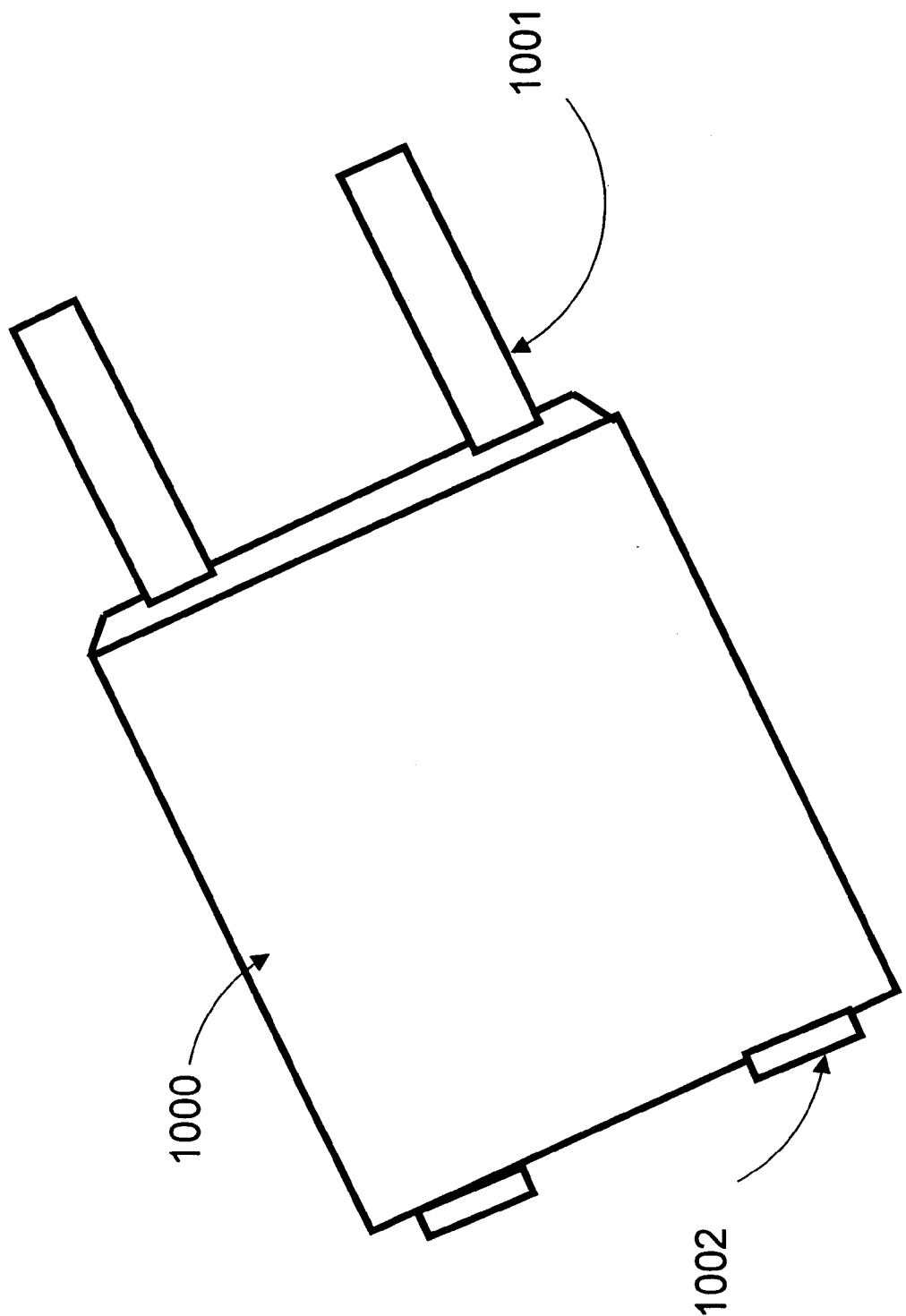
Figure 11:
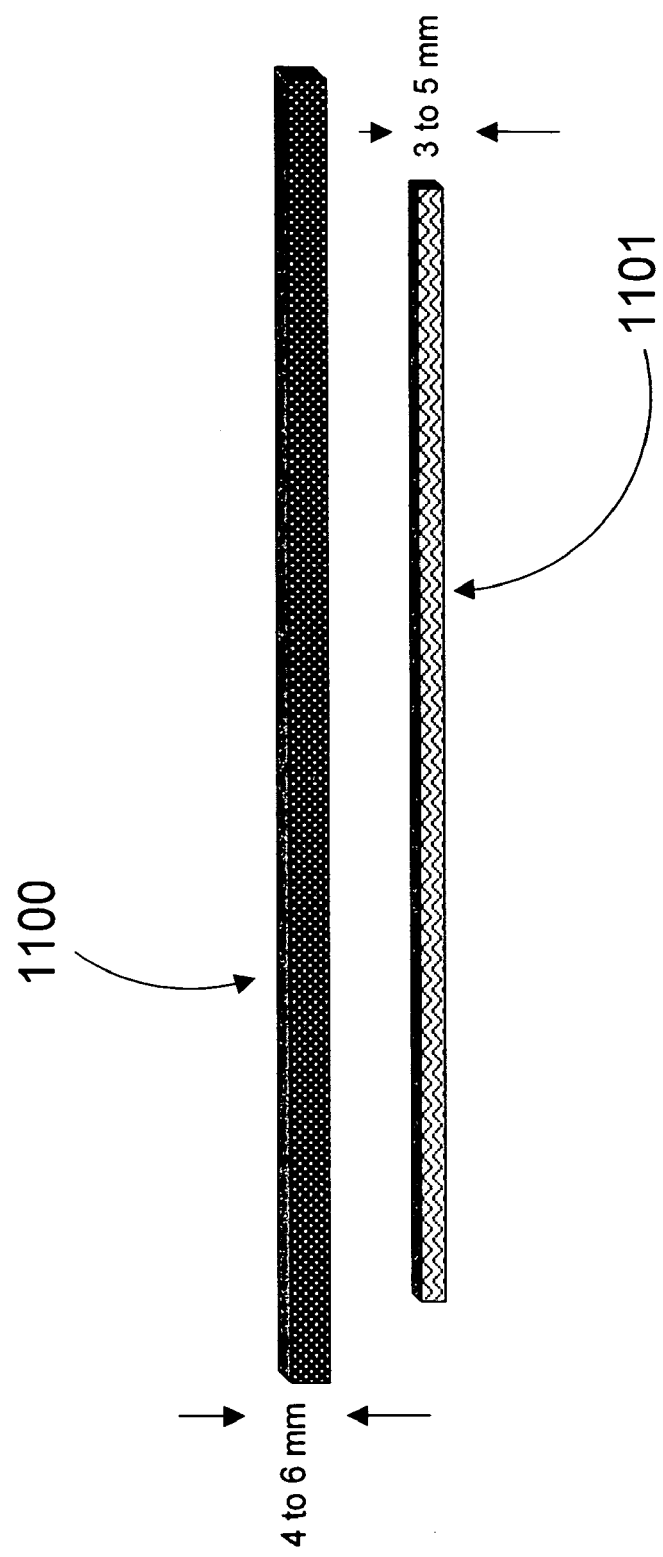
Figure 12:
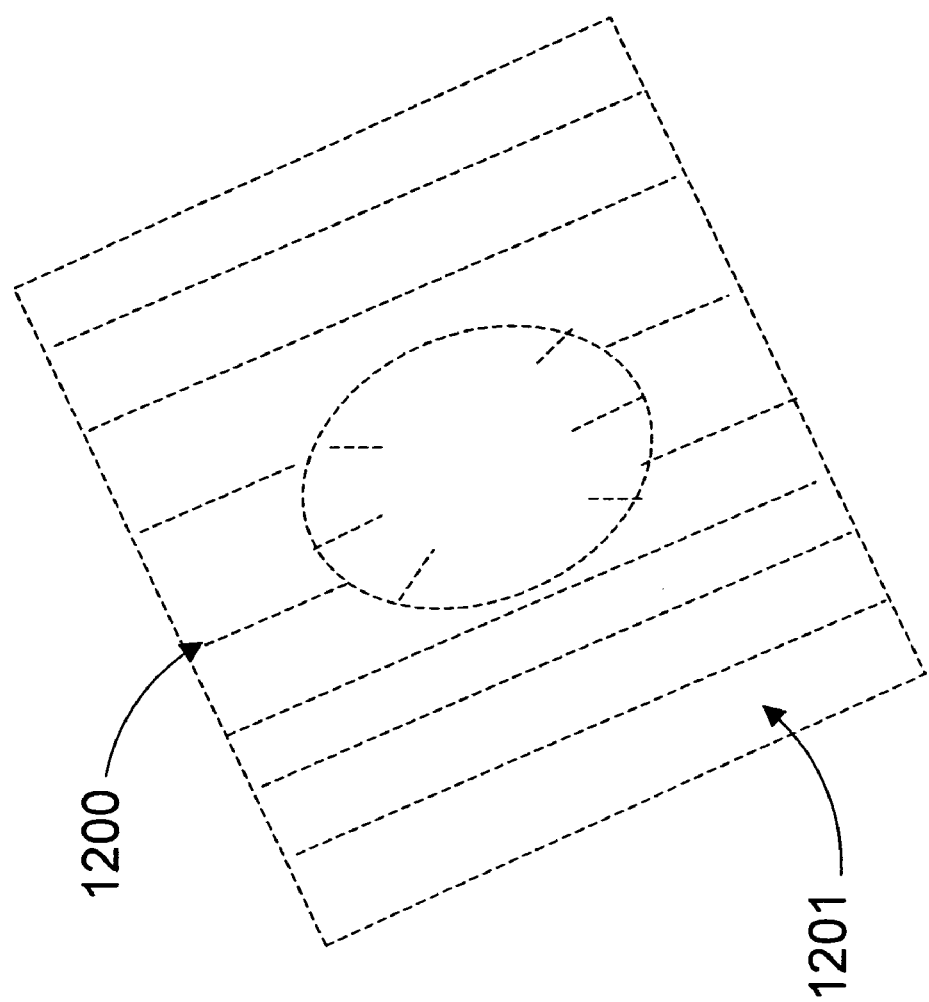
Figure 13:
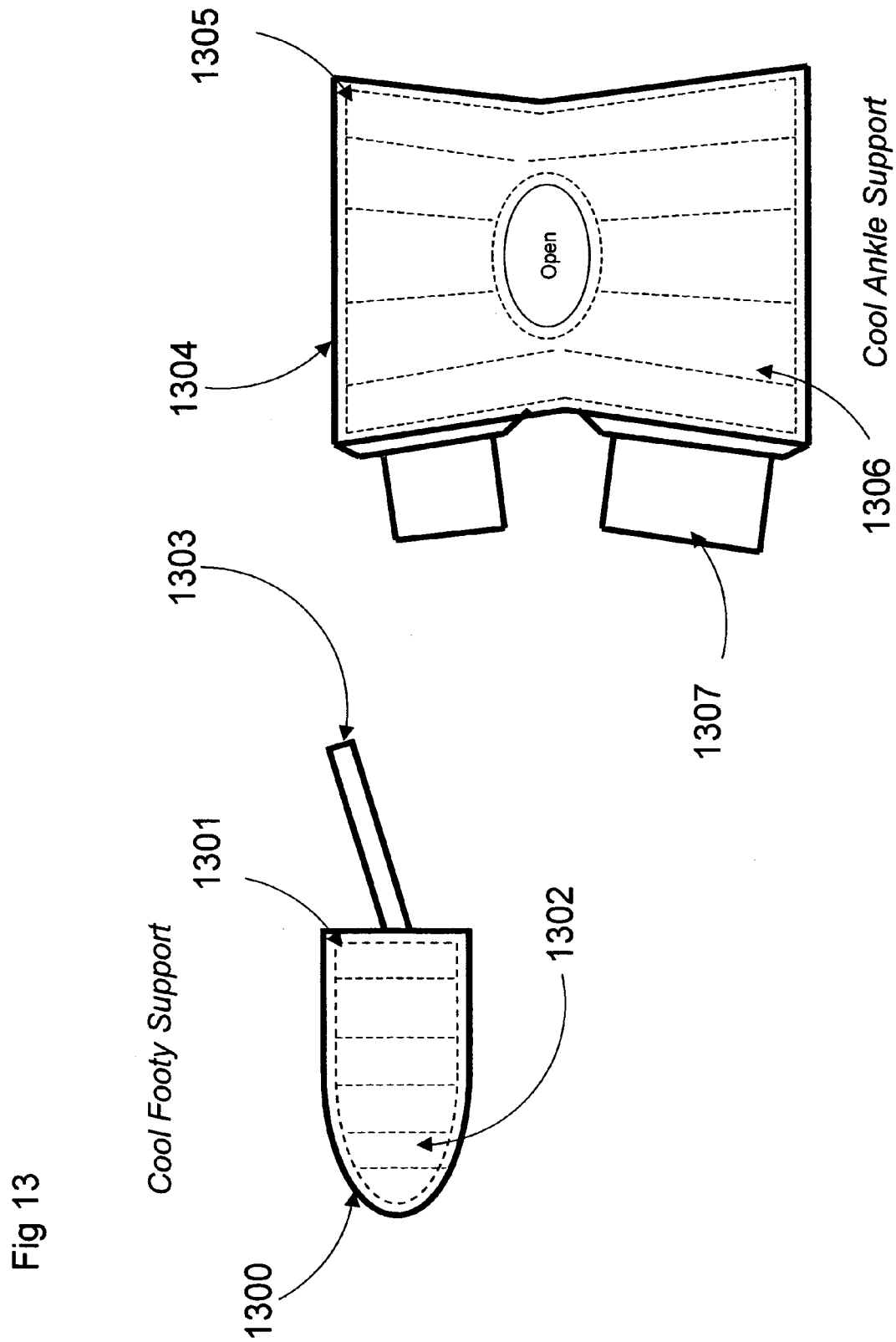
Figure 14:
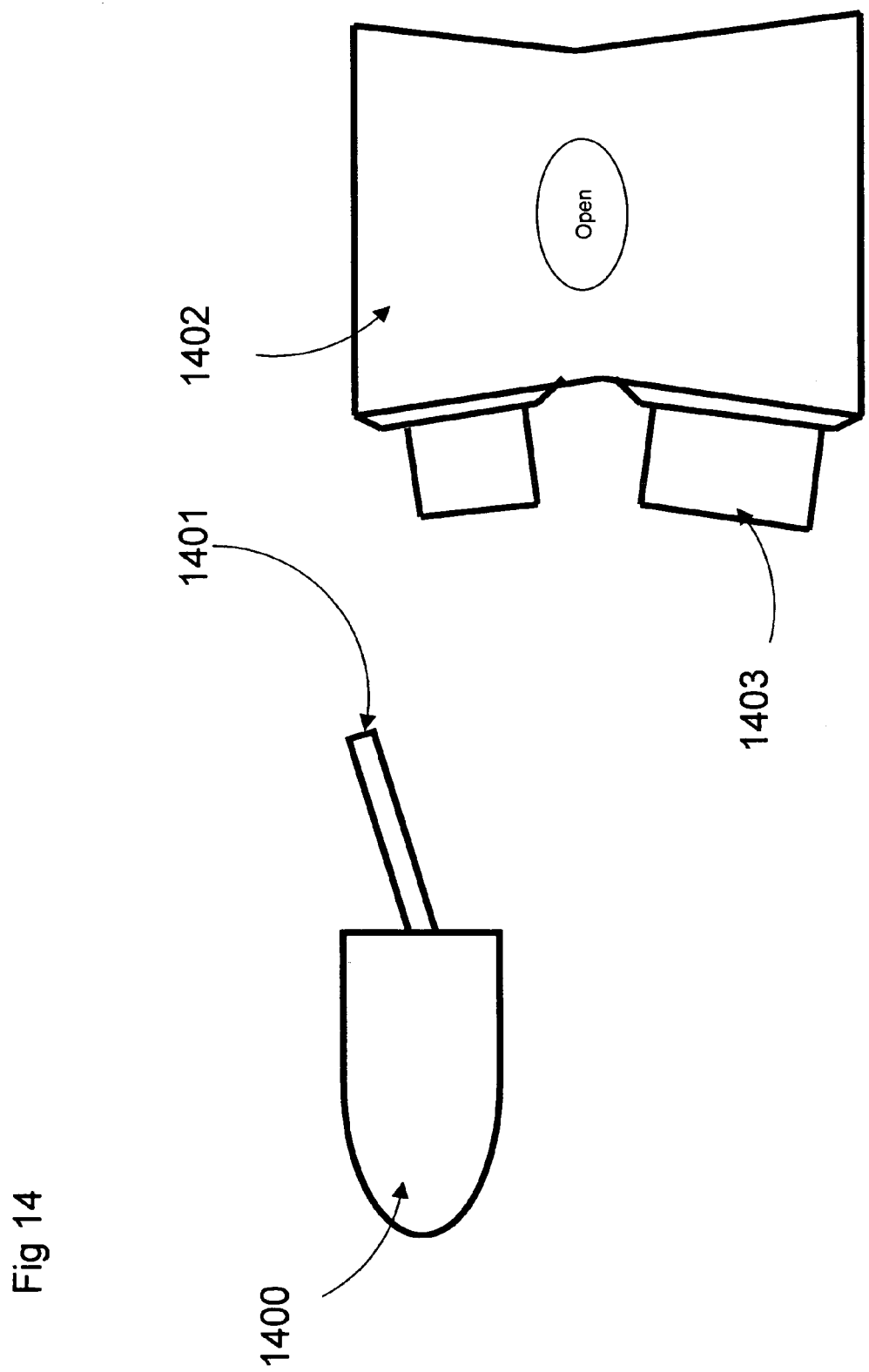
Figure 15:
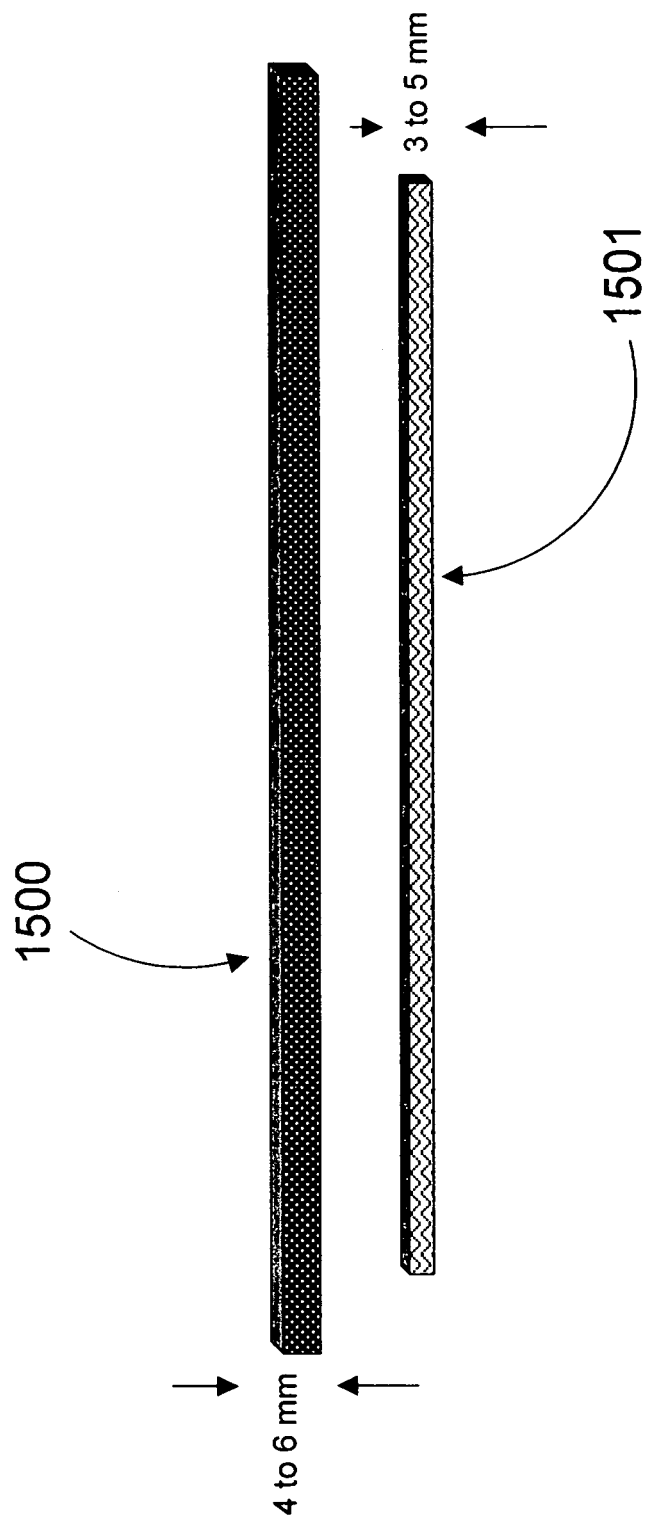
Figure 17:
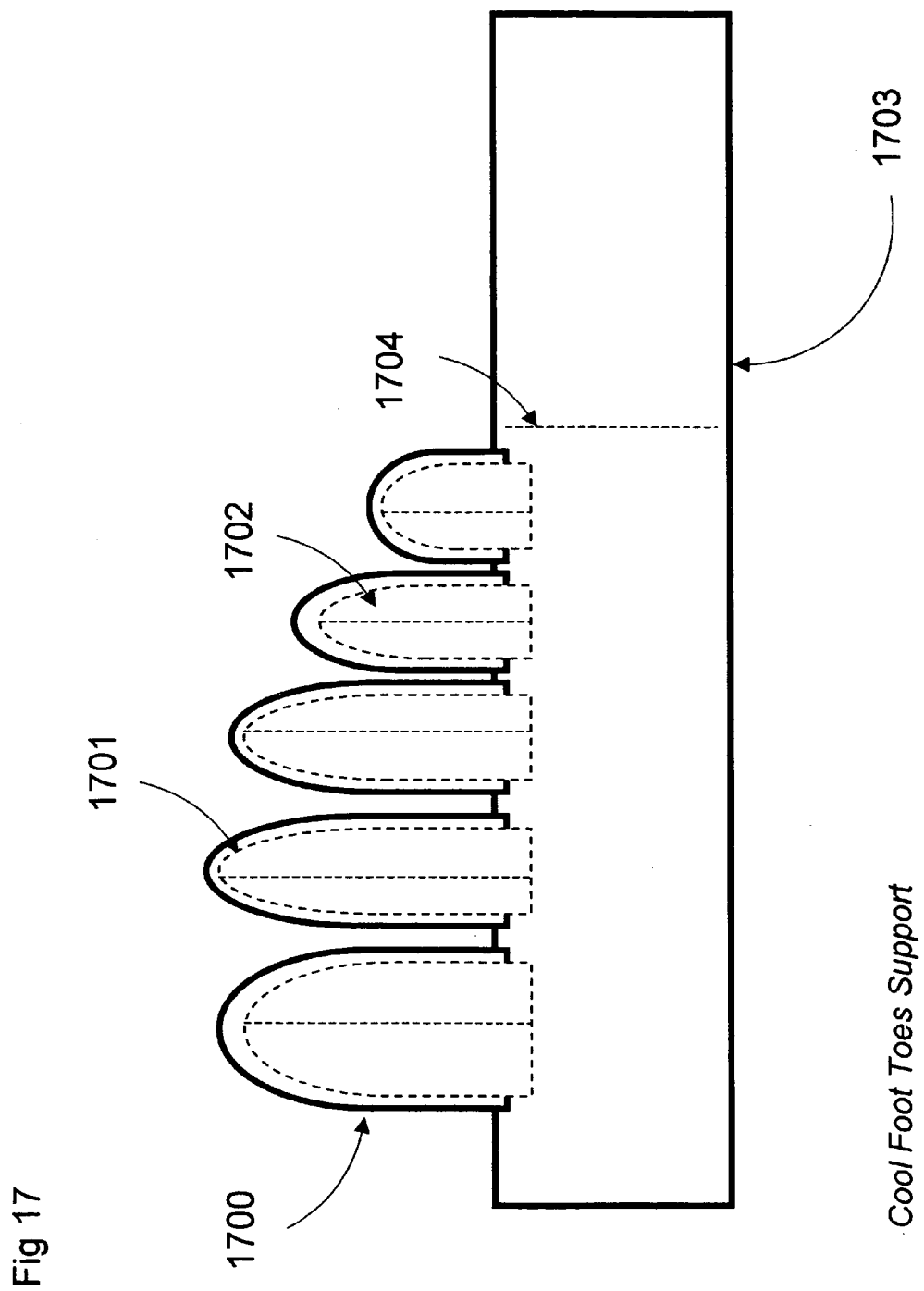
Figure 18:
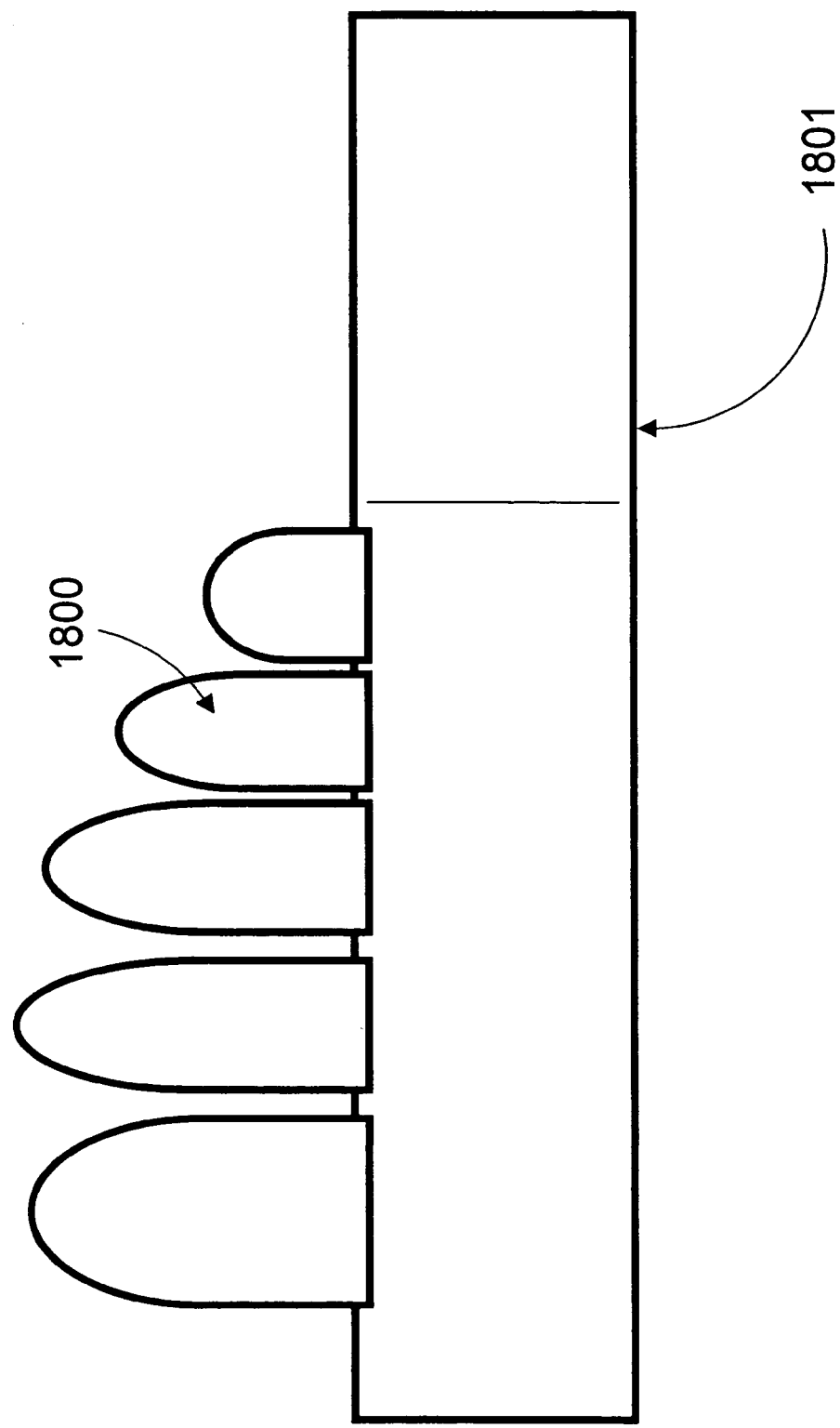
Figure 19:
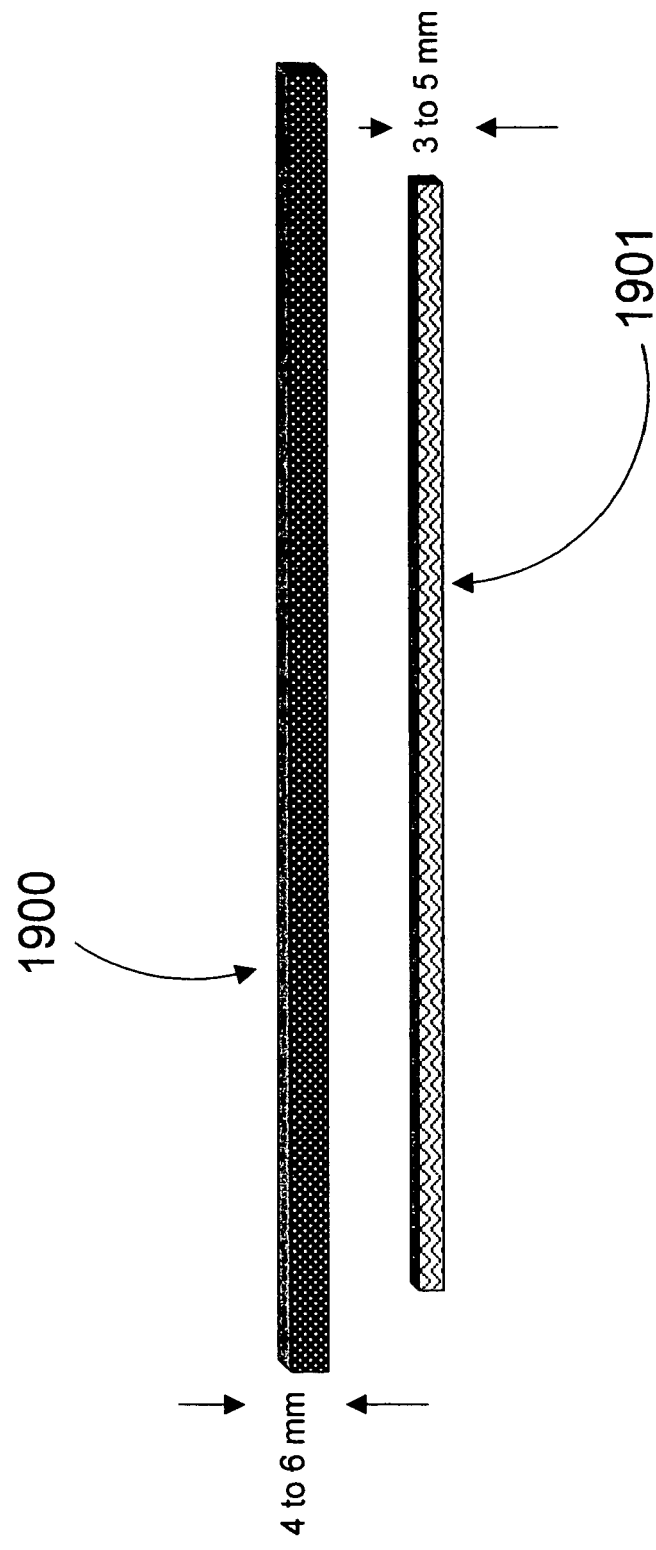
Figure 23:
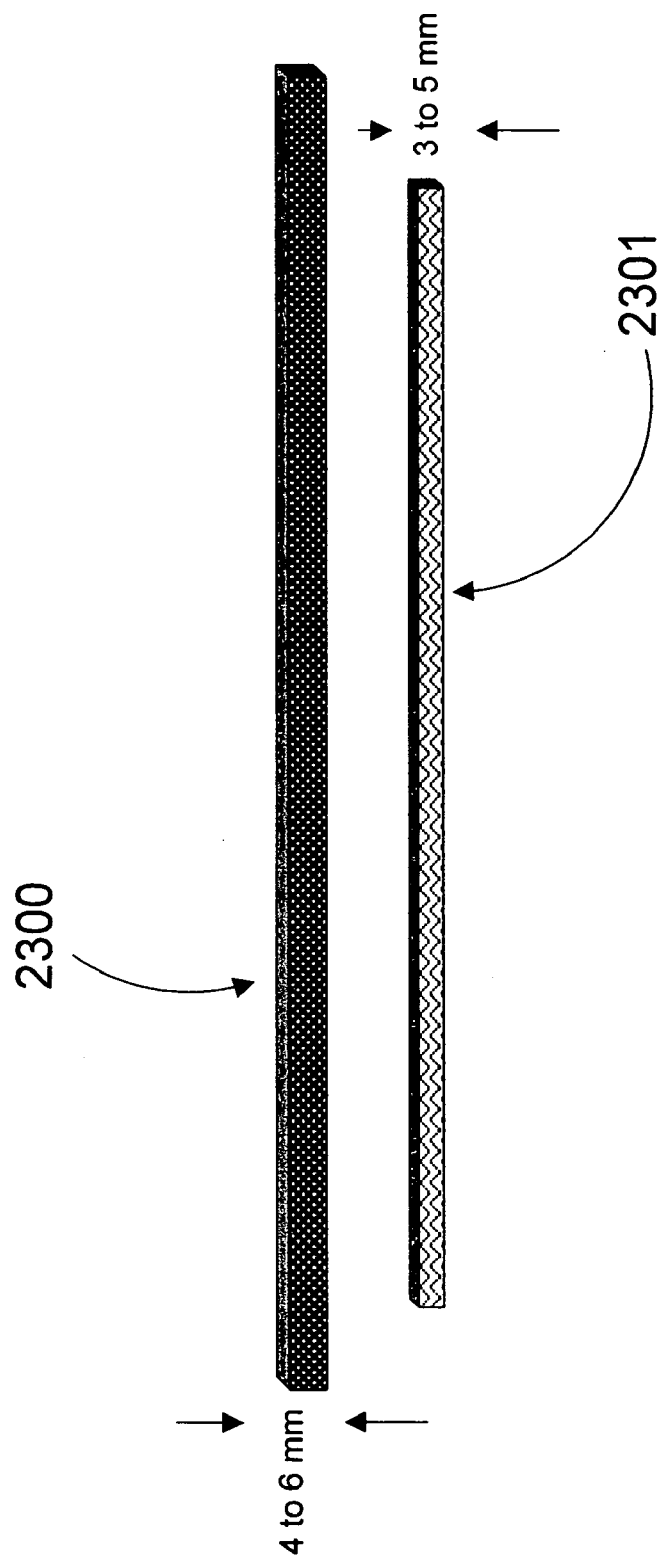
Figure 24:
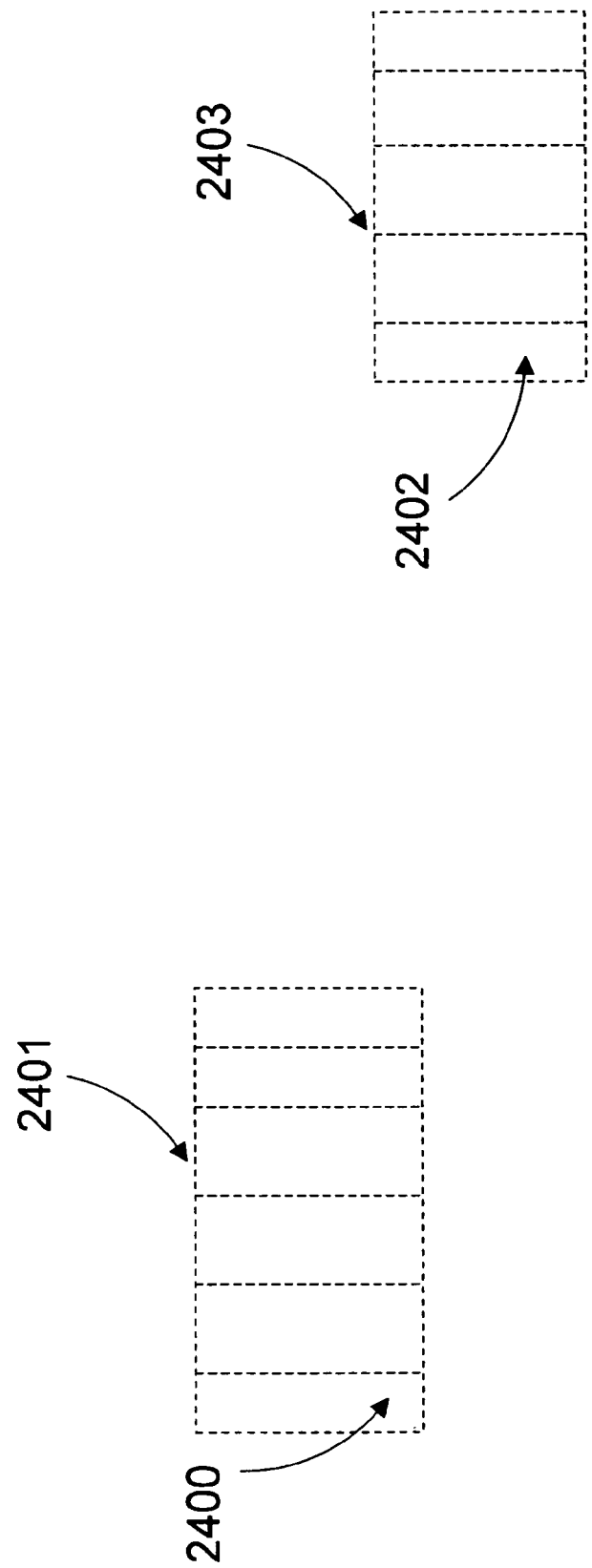
Figure 25:
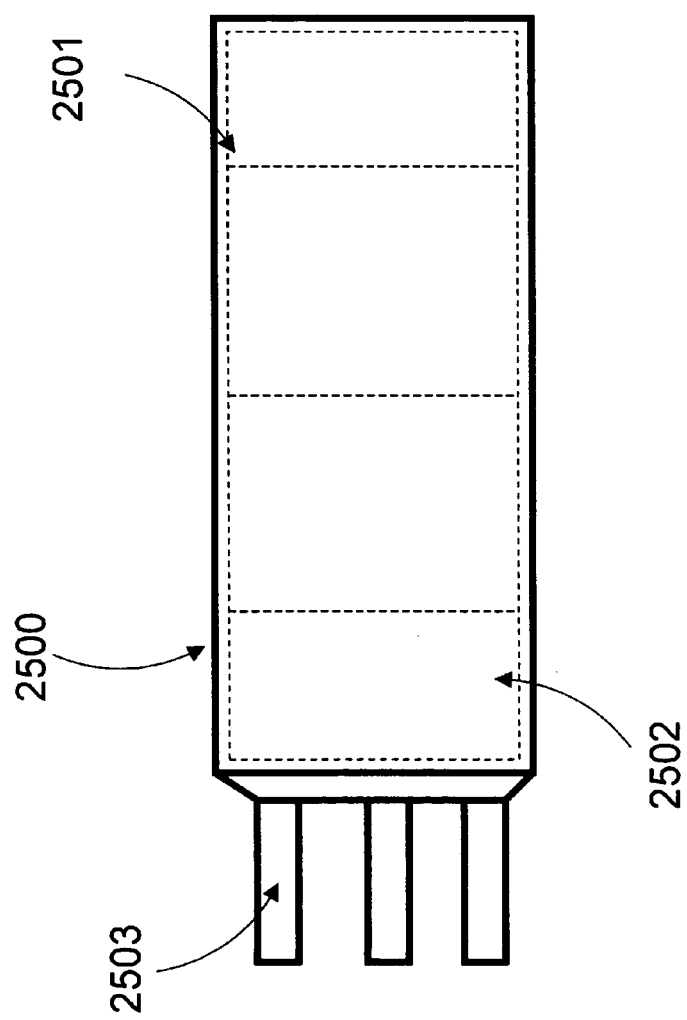
Figure 26:
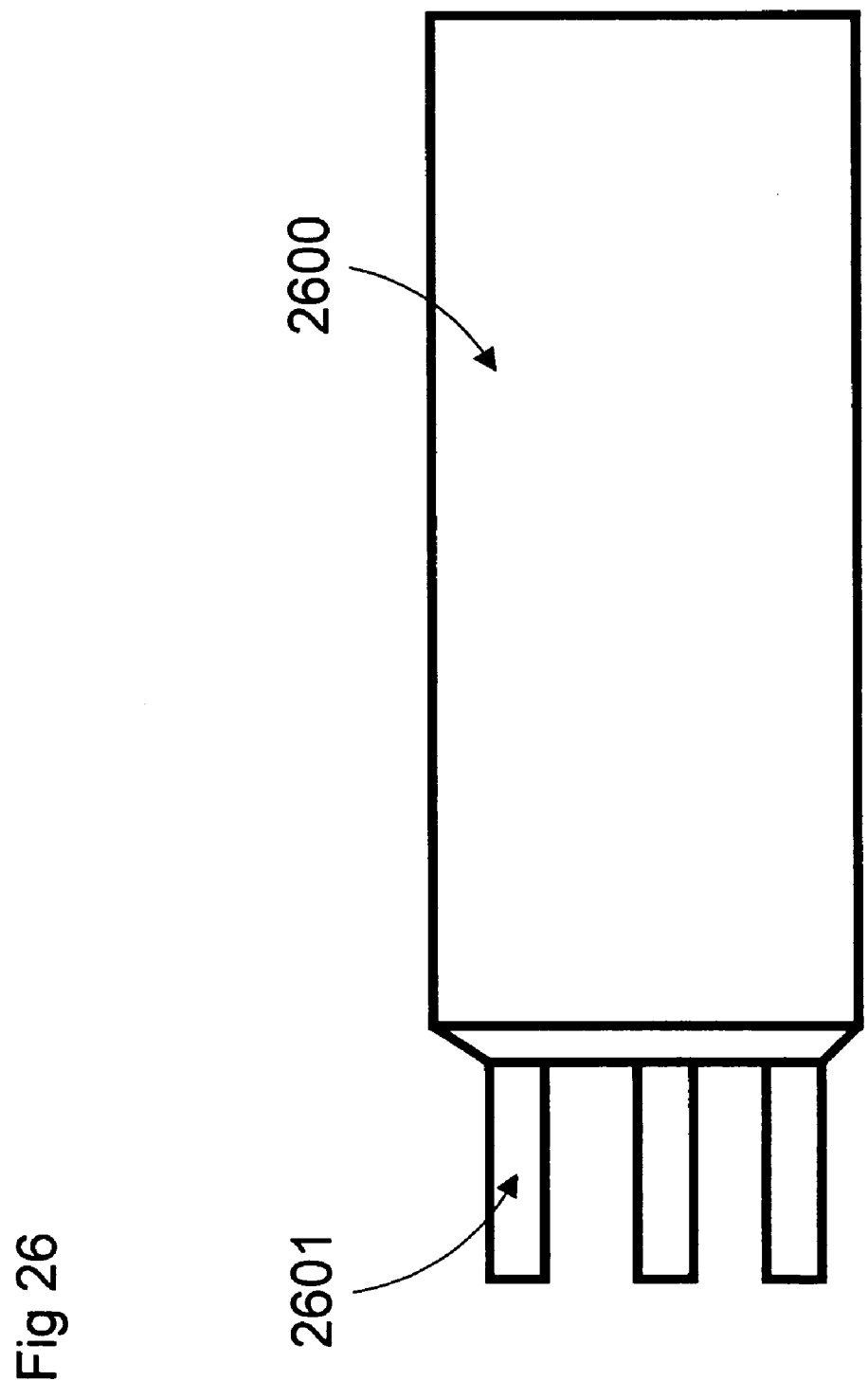
Figure 27:
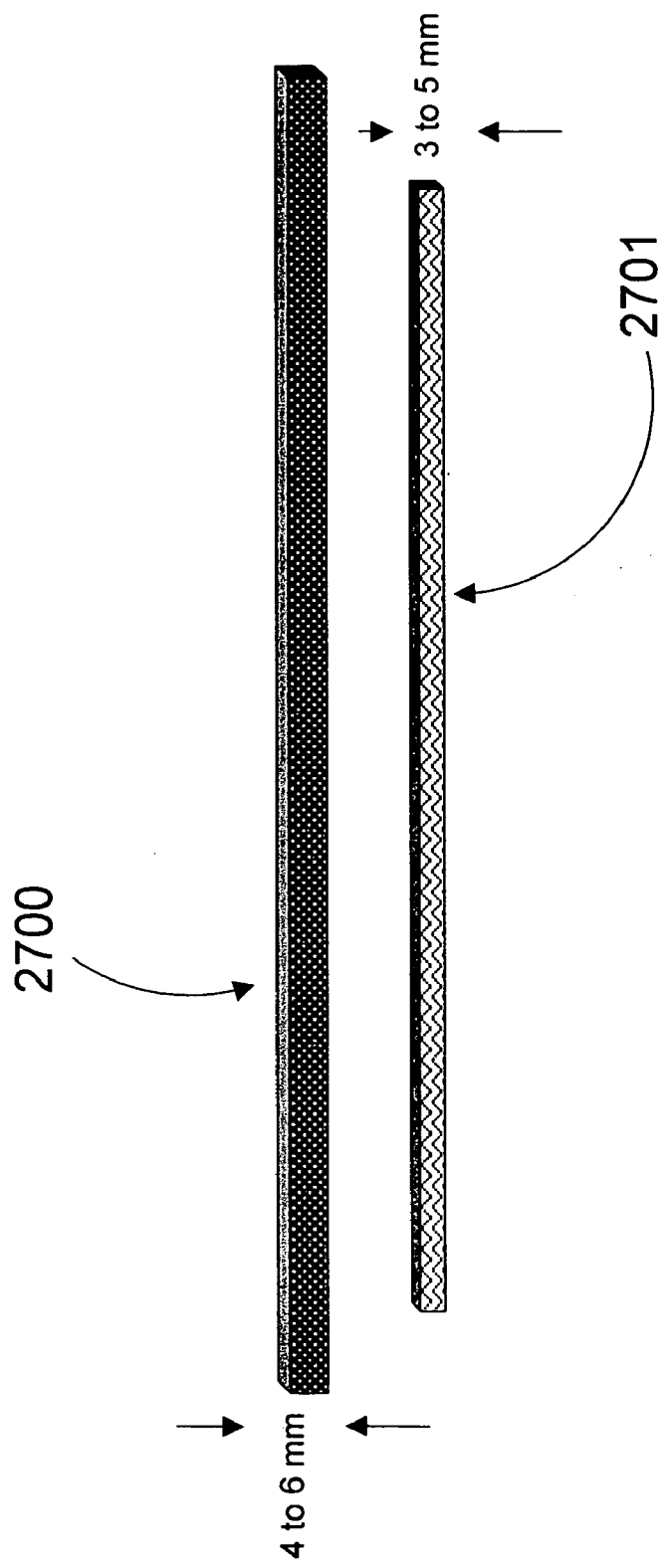
Figure 28:
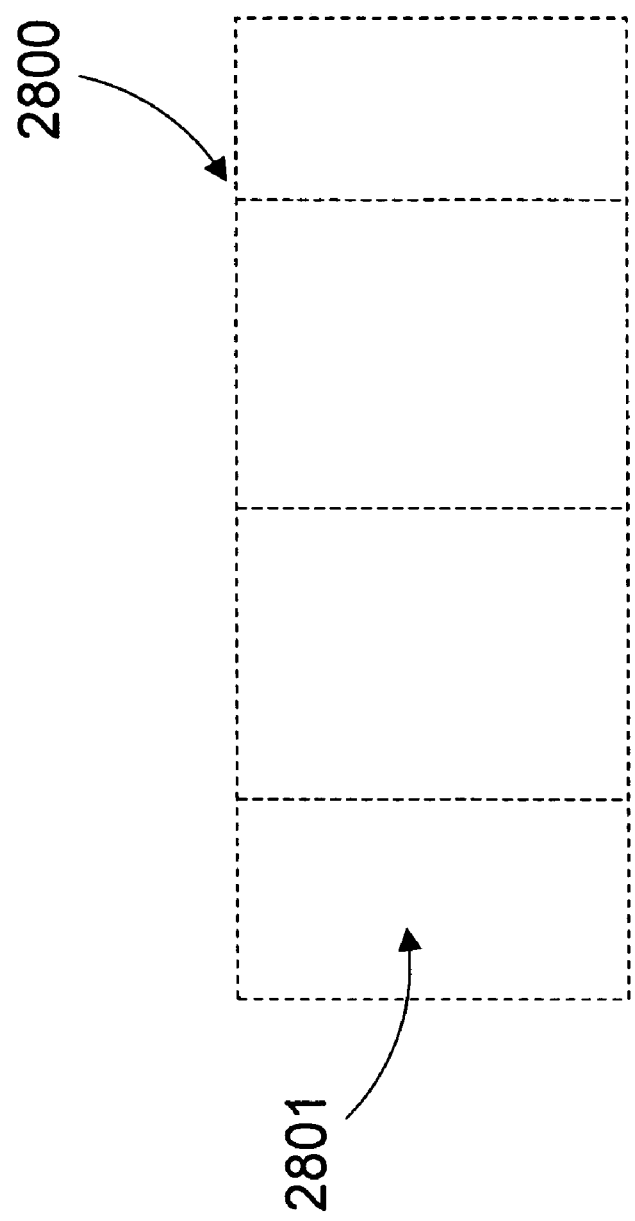
Figure 29:
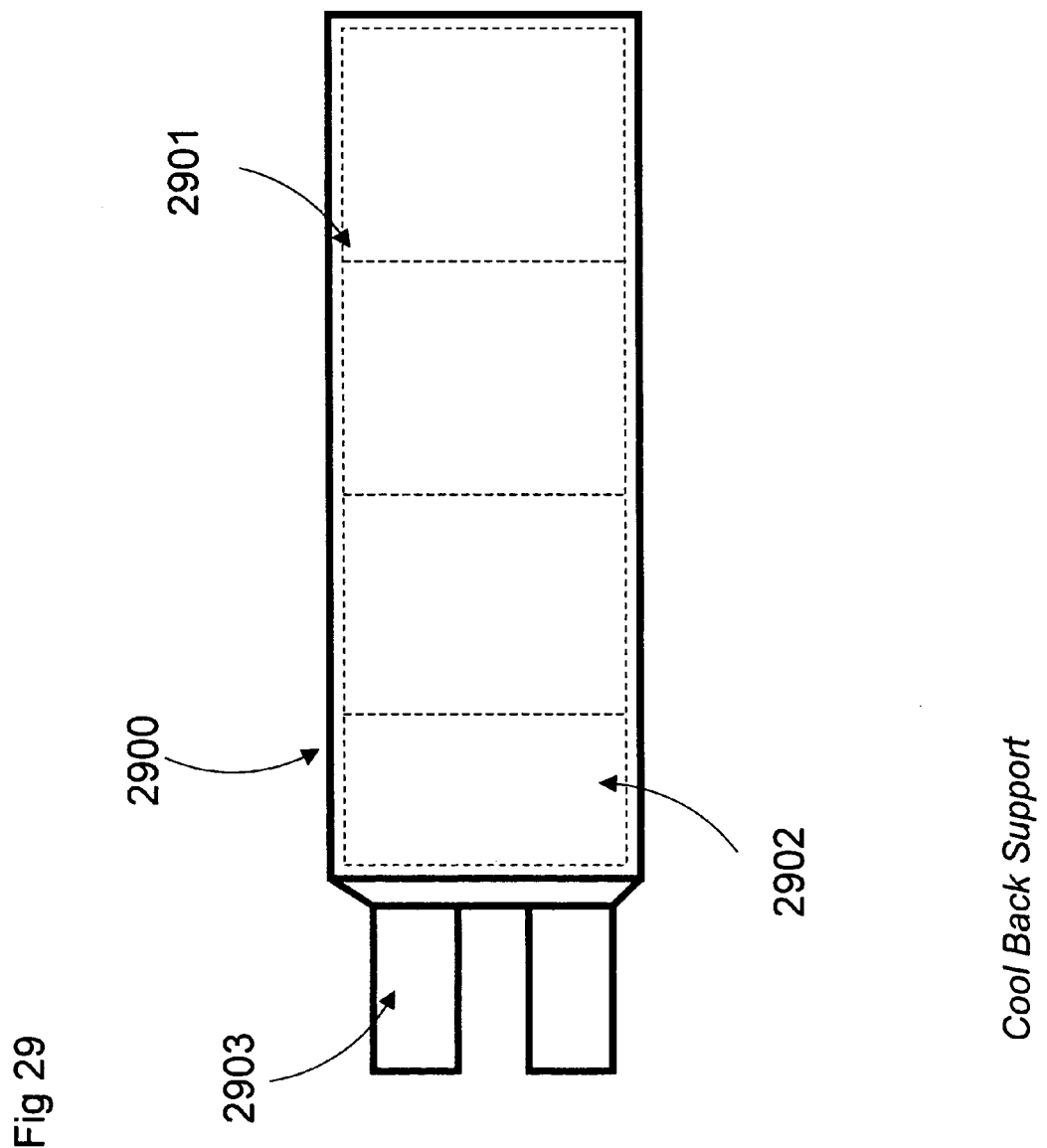
Figure 30:
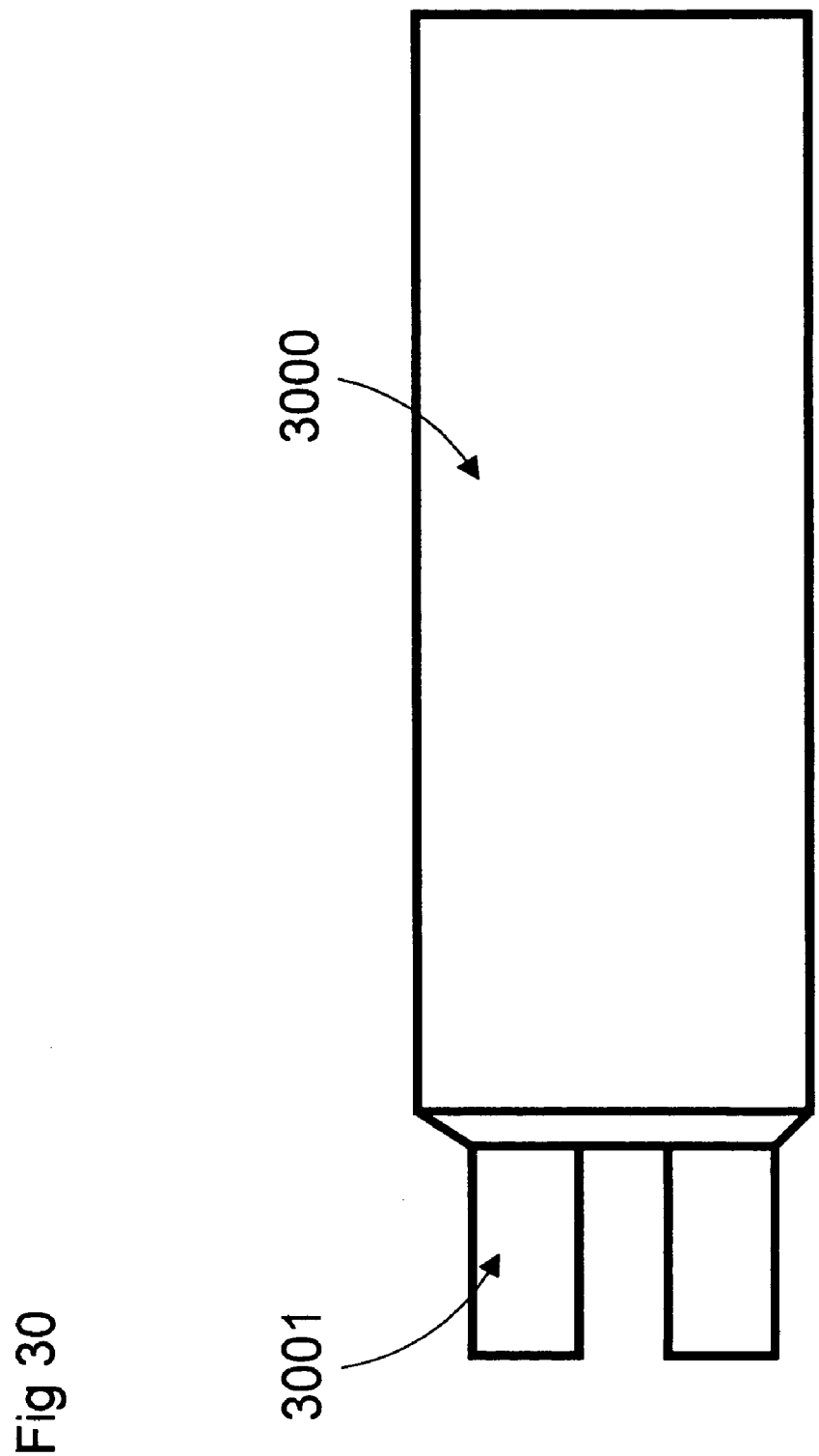
Figure 31:
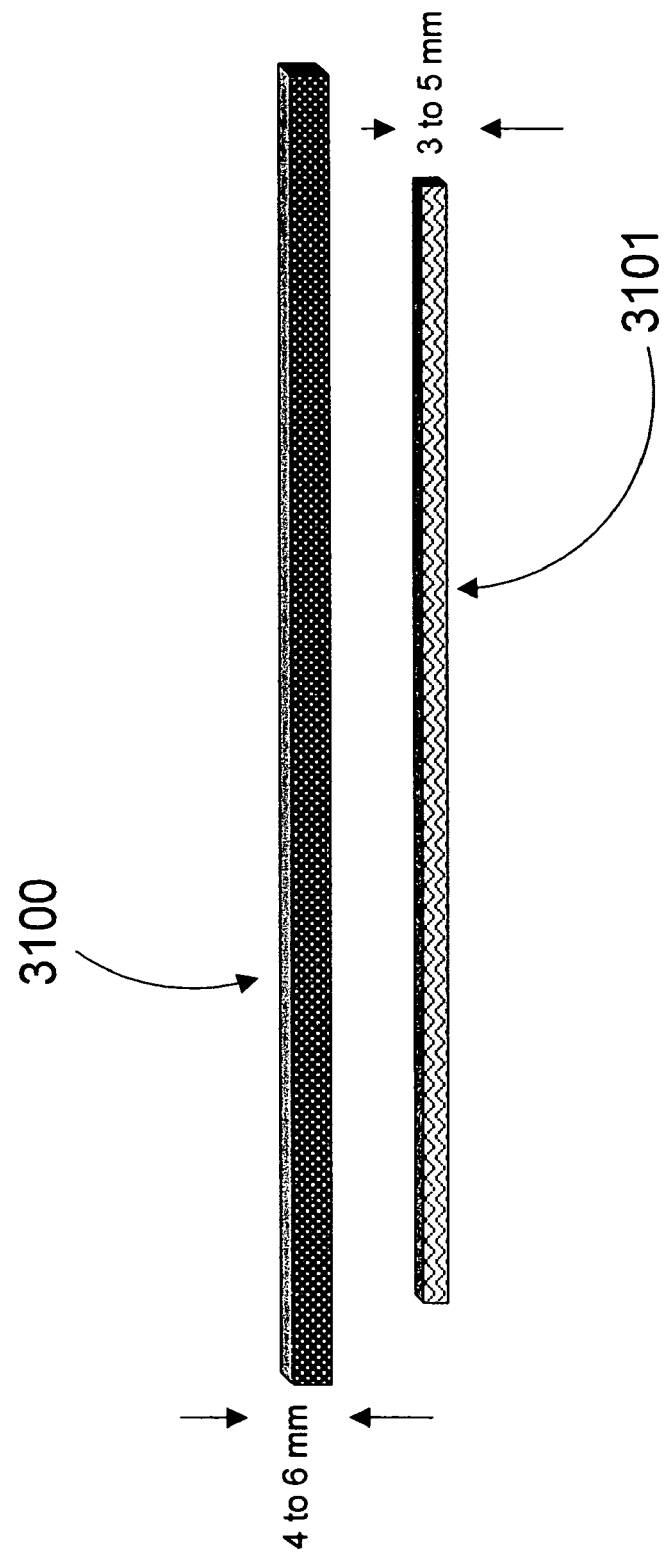
Figure 32:
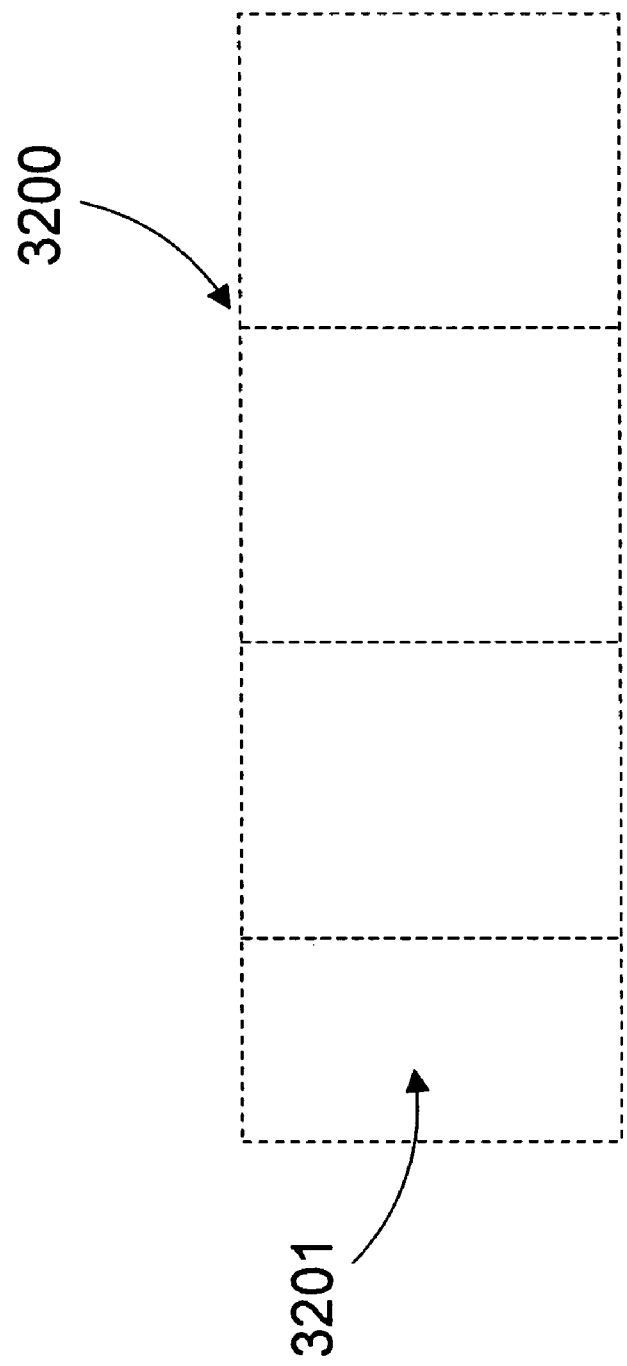
Figure 33:
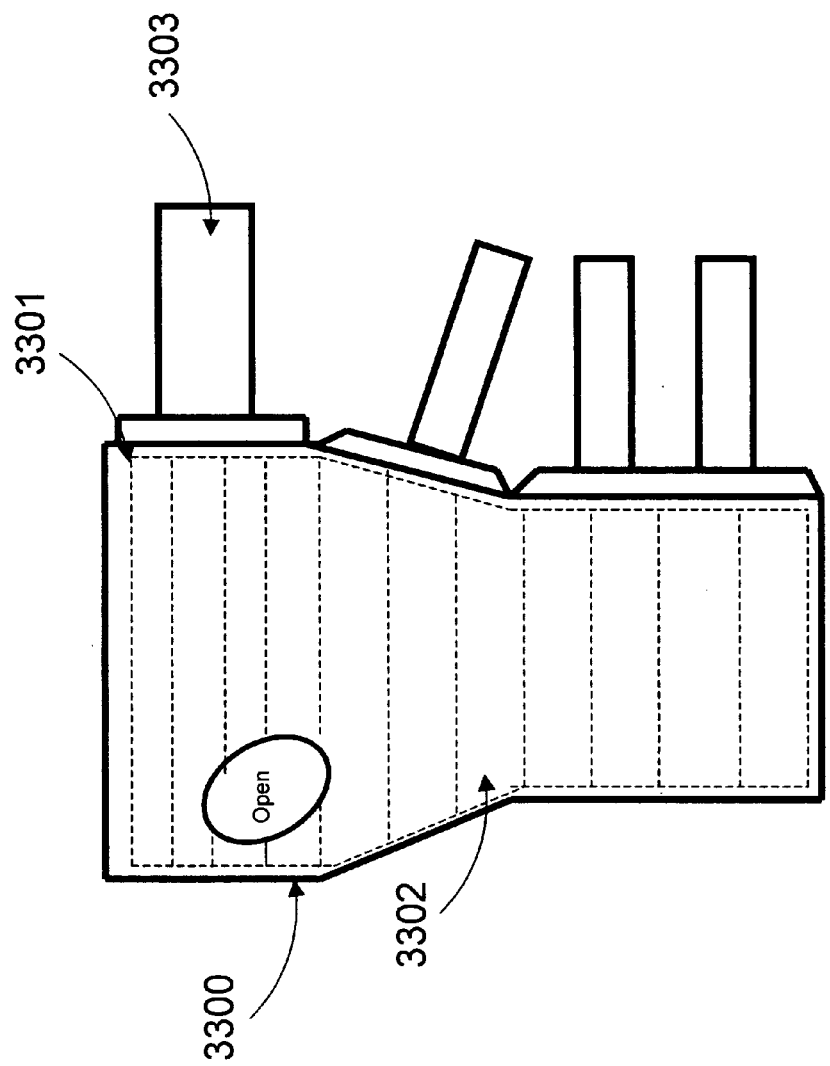
Figure 34:
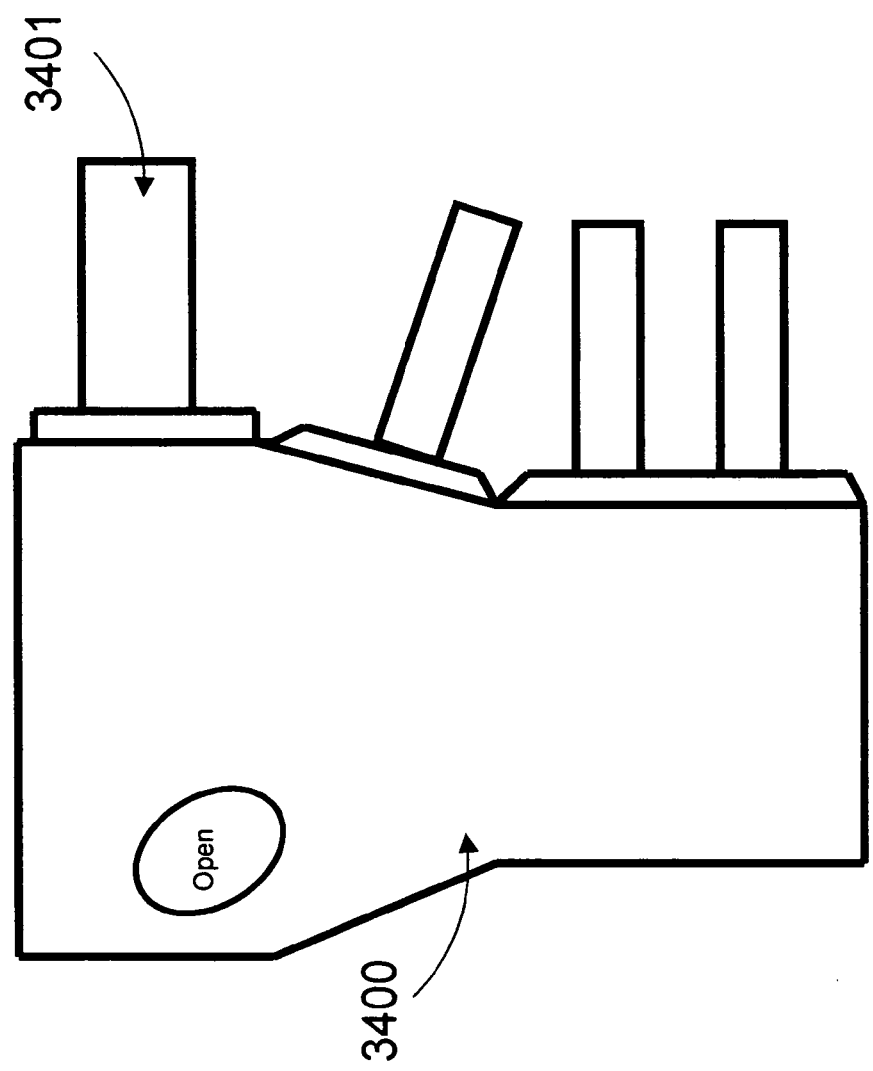
Figure 35:
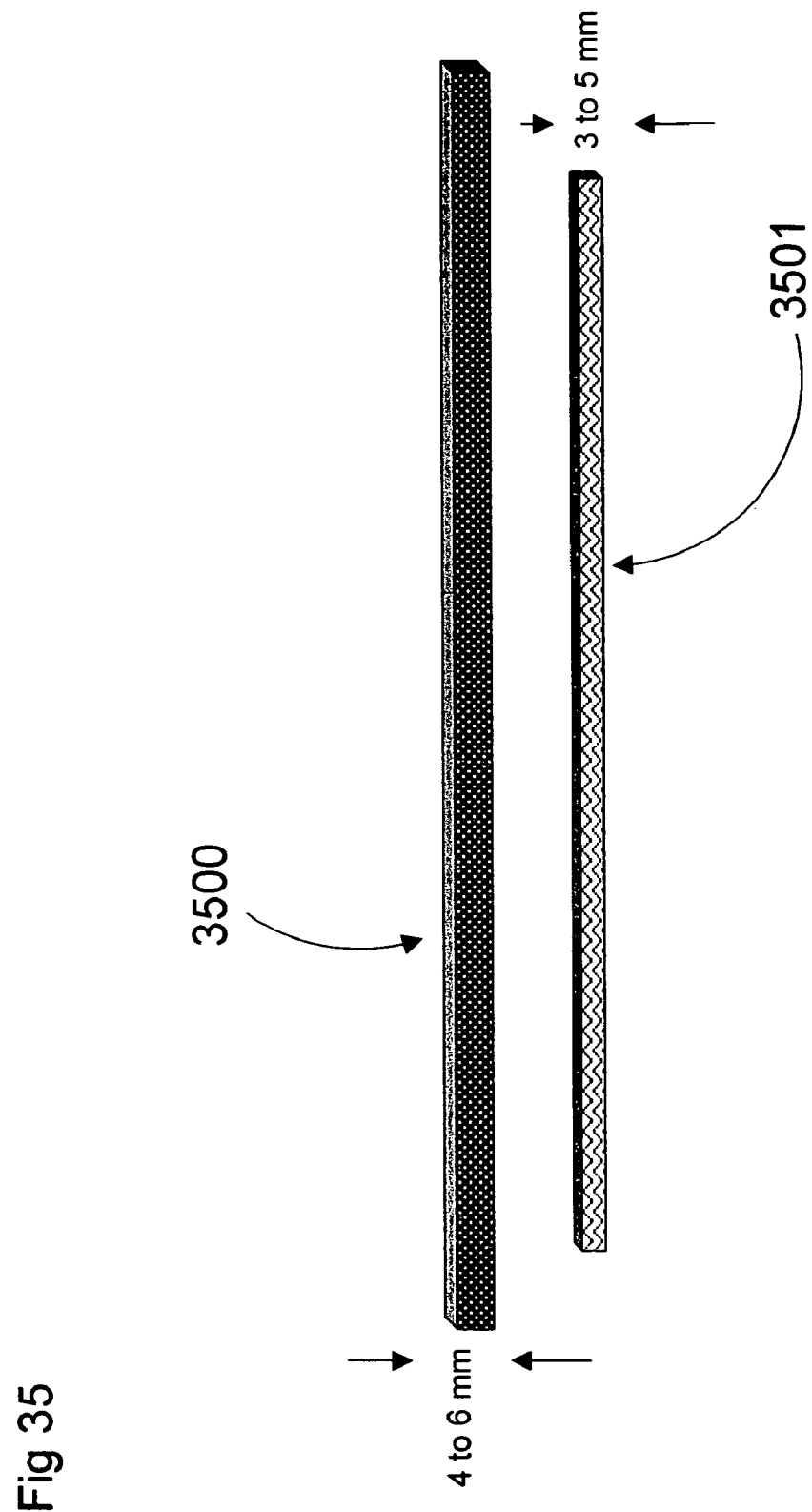
Figure 36:
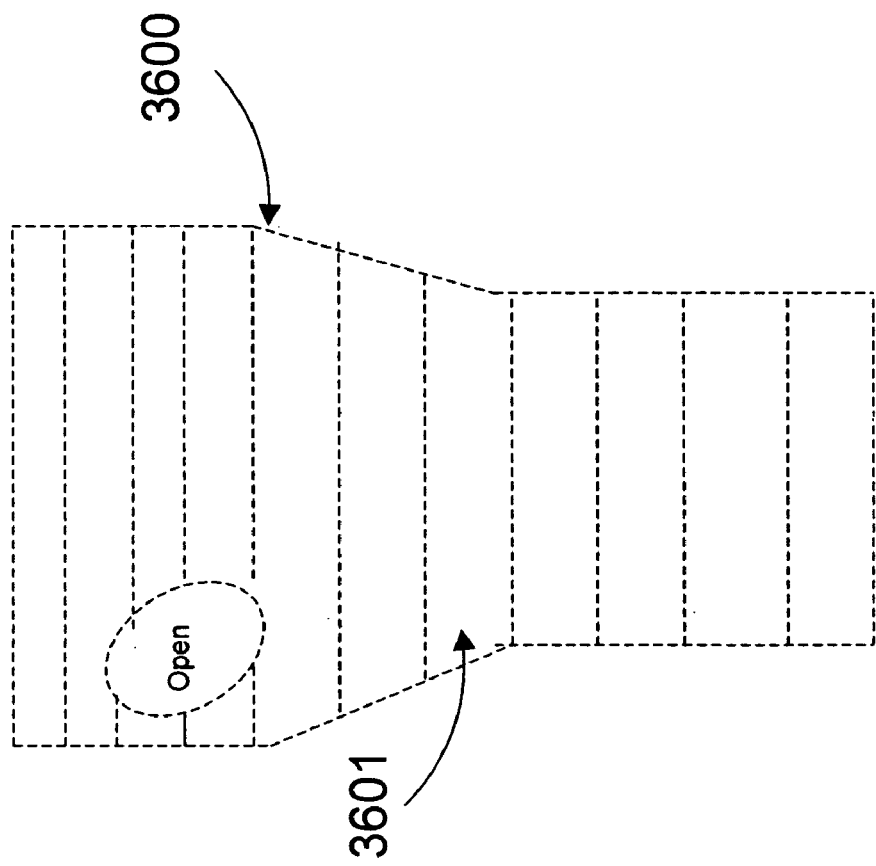
Figure 37:
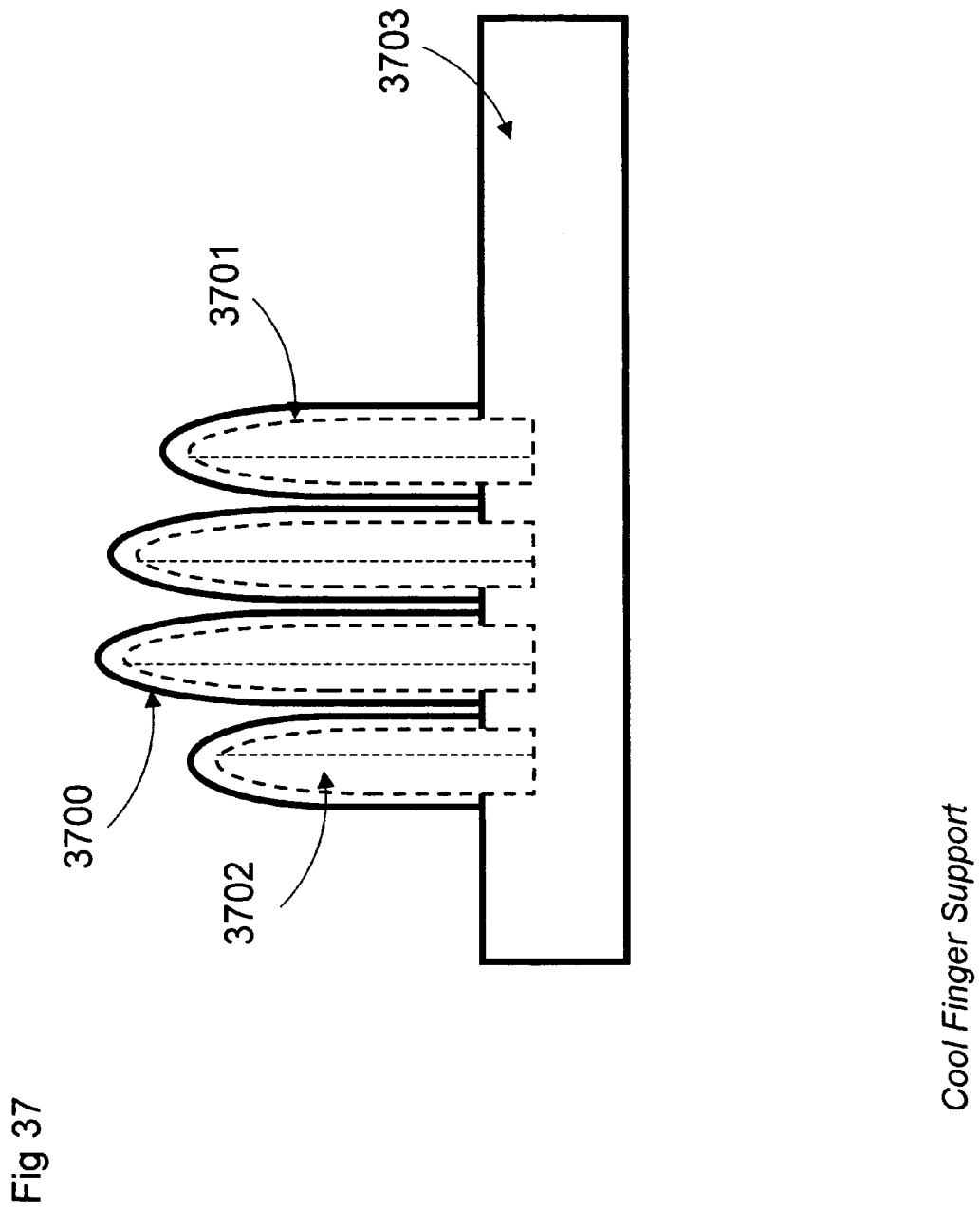
Figure 38:
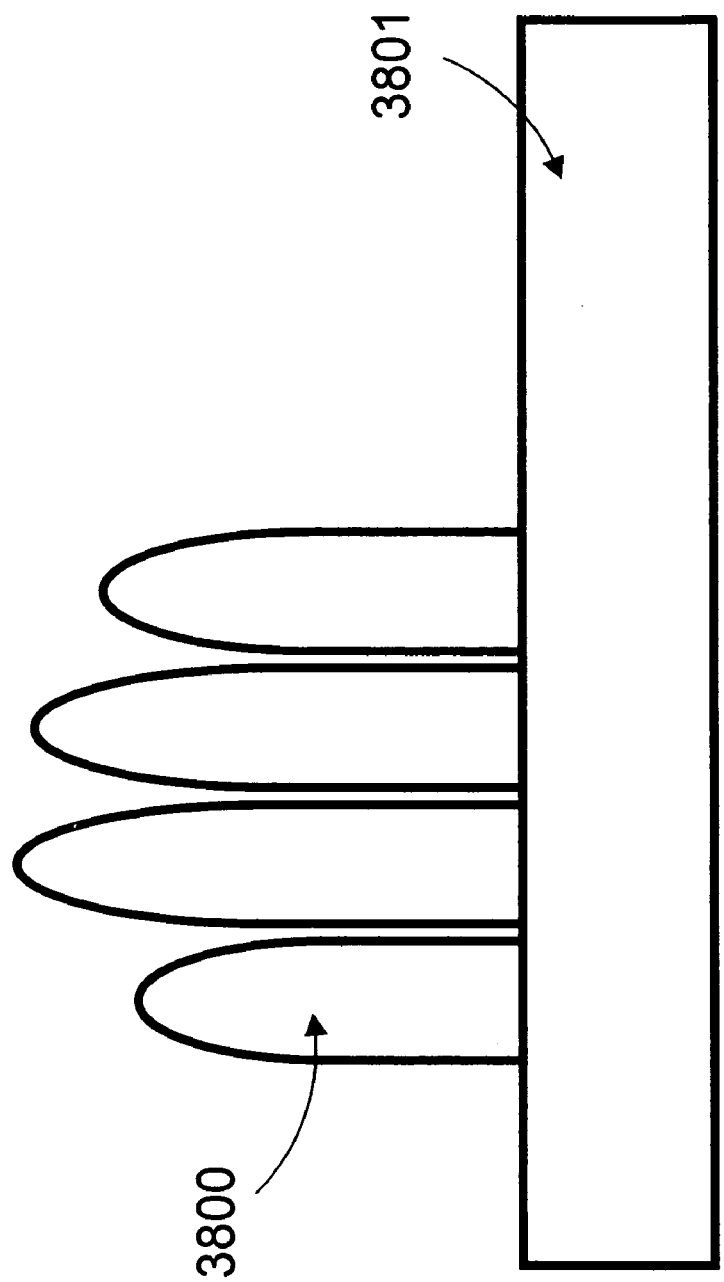
Figure 39:
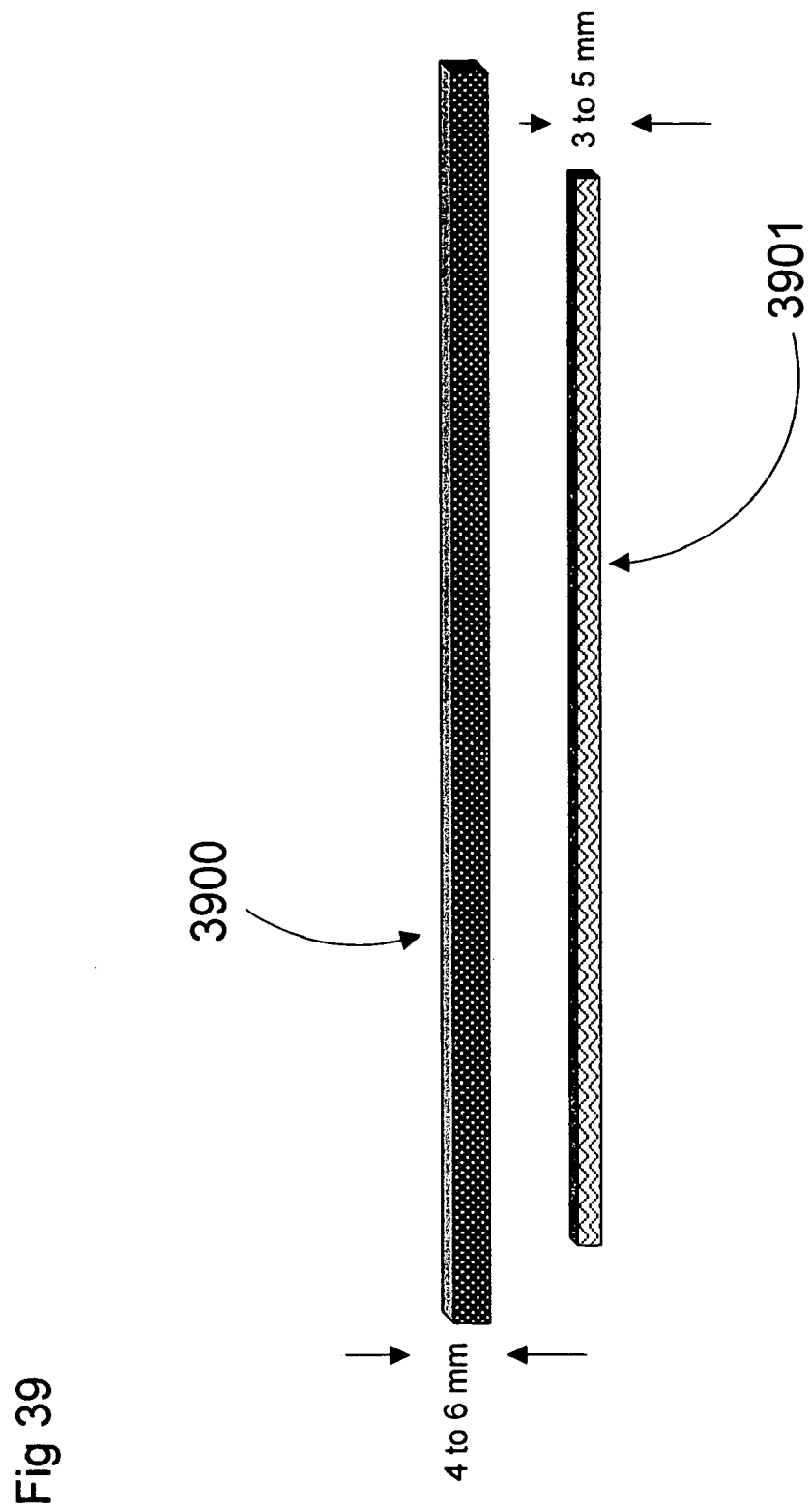
Figure 40:
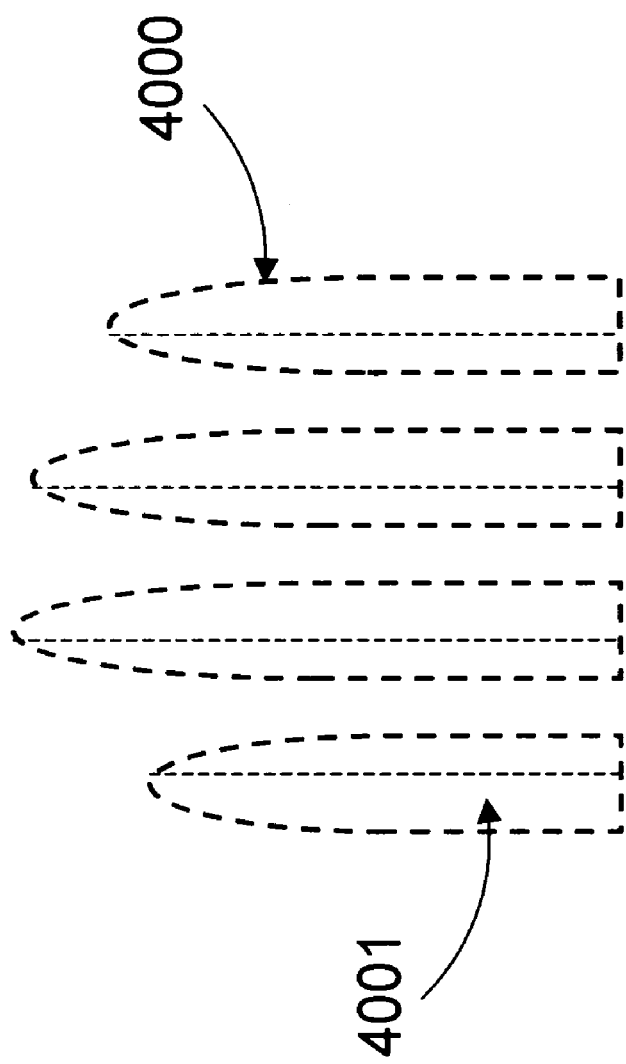
Figure 41:
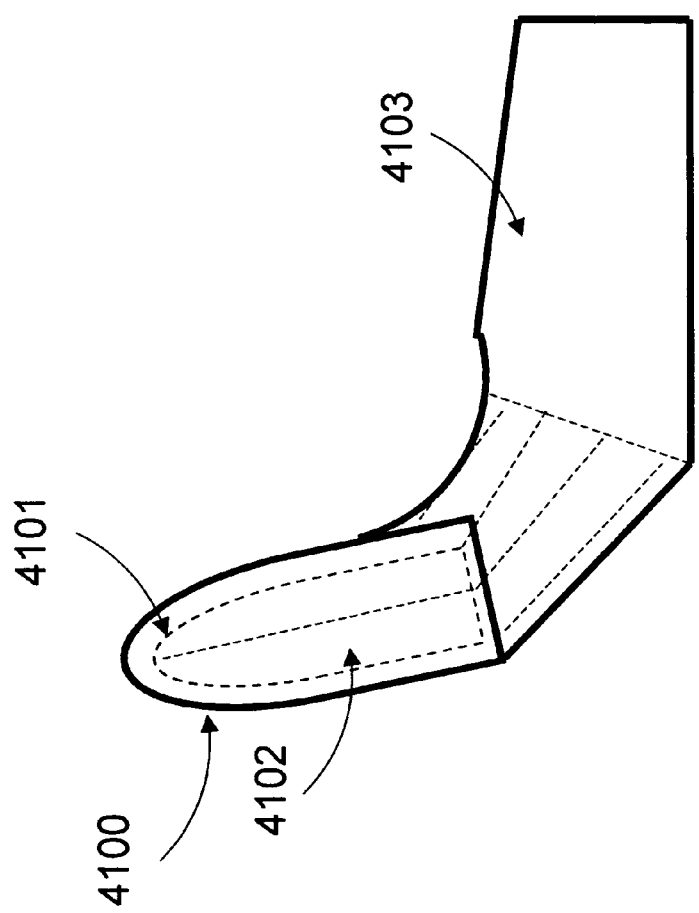
Figure 42:
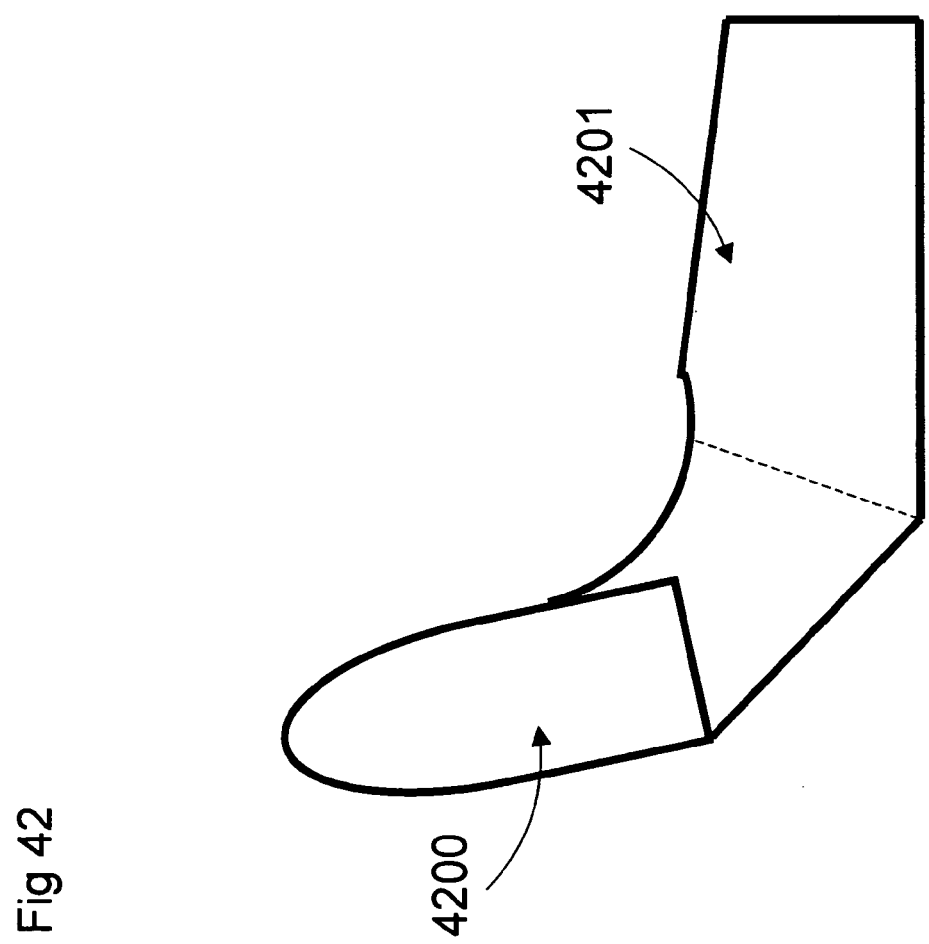
Figure 43:
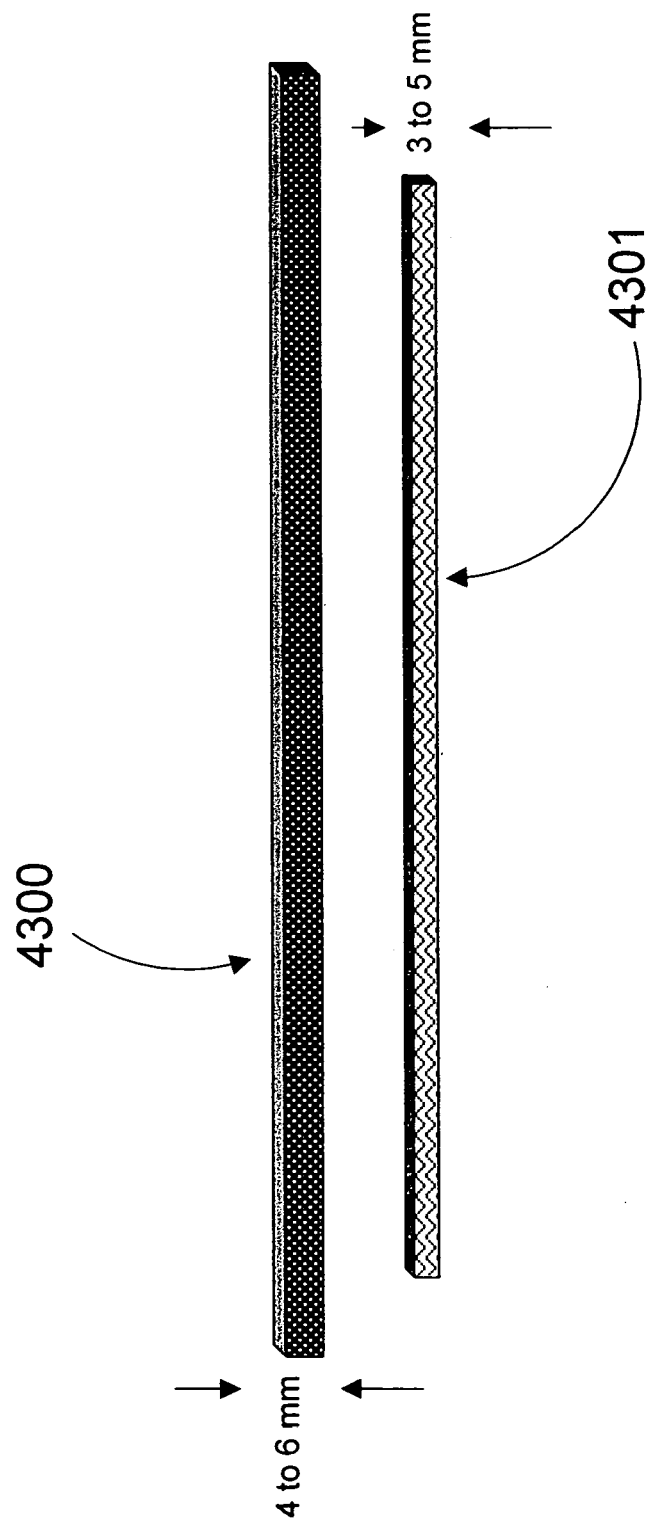
Figure 44:
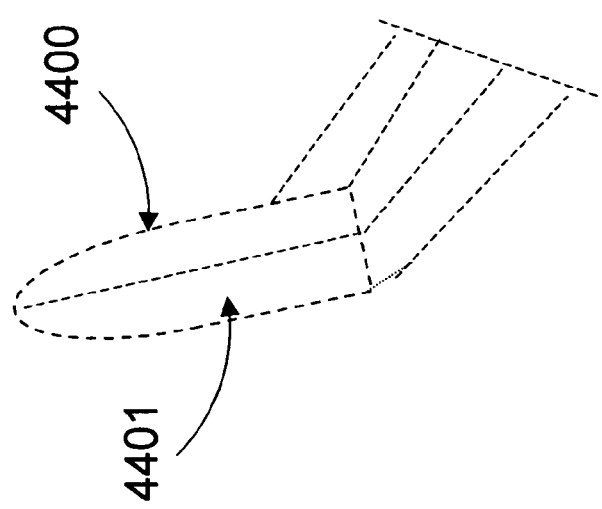

Referring to FIG. 4, the cool gel packet 400 of the health care device is a latex material 3 to 5 mm. in thickness with separate chambers 401 that holds the chemical solution providing a cooling sensation that can sustain itself for 15 to 30 minutes.

Referring to FIGS. 5–44, as part of the embodiment of the patent.

What is claimed is:

1. A product to help reduce/decrease, prevent and avoid swelling/edema to all joints and soft tissue areas of the body by providing cooling functionality to all joints and soft tissue areas, comprising: a neoprene wrap forming a strap and individual capsules, wherein the capsules are all connected to the strap along a single edge so that all or one toe may be individually placed into the capsules and the strap may be wrapped around the user's foot sole and dorsal, and a liquid contained in individual latex bags, wherein the liquid provides the cooling function and the latex bags are stitched into each individual capsule of the neoprene wrap to cover one or more toes and further wherein the latex bags operate by cooling the liquid in a 32 degree environment until the liquid gels for use.

2. A product to help reduce/decrease, prevent and avoid swelling/edema to all joints and soft tissue areas of the body by providing cooling functionality to all joints and soft tissue areas, comprising: a neoprene wrap forming a strap and individual capsules, wherein the capsules are all connected to the strap along a single side so that all or one finger may be individually placed into the capsules and the strap may be wrapped around the user's hand/palm, and a liquid contained in individual latex bags, wherein the liquid provides the cooling function and the latex bags are stitched into each individual capsule of the neoprene wrap to cover one or more fingers and further wherein the latex bags operate by freezing the liquid in a 32 degree environment until the liquid gels for use.

3. A product according to claim 1 or 2, wherein each latex bag comprises two single layers coupled together to define a cavity wherein the liquid is stored and the area of the bags is less than the area of the neoprene wrap.

4. A product according to claim 1 or 2, wherein the liquid may gel but will not freeze at 32° F.

5. A product according to claim 1 or 2, wherein the latex bags conform to the particular joints and soft tissue area being treated.

\* \* \* \* \*